(12) United States Patent
Heatherington

(10) Patent No.: US 11,925,760 B2
(45) Date of Patent: Mar. 12, 2024

(54) RESPIRATORY ASSEMBLY AND METHODS OF USING THE SAME

(71) Applicant: SNAP CPAP, LLC, Chapel Hill, NC (US)

(72) Inventor: Stuart Heatherington, Chapel Hill, NC (US)

(73) Assignee: SNAP CPAP, LLC, Chapel Hill, NC (US)

(*) Notice: Subject to any disclaimer, the term of this patent is extended or adjusted under 35 U.S.C. 154(b) by 823 days.

(21) Appl. No.: 16/925,894

(22) Filed: Jul. 10, 2020

(65) Prior Publication Data

US 2021/0008318 A1 Jan. 14, 2021

Related U.S. Application Data

(63) Continuation of application No. PCT/US2020/038944, filed on Jun. 22, 2020.
(Continued)

(51) Int. Cl.
*A61M 16/06* (2006.01)
*A61M 16/00* (2006.01)
(Continued)

(52) U.S. Cl.
CPC .... *A61M 16/0666* (2013.01); *A61M 16/0057* (2013.01); *A61M 16/0816* (2013.01);
(Continued)

(58) Field of Classification Search
CPC .......... A61M 16/0057; A61M 16/0666; A61M 16/0683; A61M 16/0688; A61M 16/0816;
(Continued)

(56) References Cited

U.S. PATENT DOCUMENTS 7,793,987 B1 * 9/2010 Busch .................. A61M 16/161
285/9.1
8,887,725 B2 11/2014 Hernandez et al.
(Continued)

FOREIGN PATENT DOCUMENTS

JP 2018530389 A 10/2018
WO 2017062677 A1 4/2017
(Continued)

OTHER PUBLICATIONS

WIPO; International Preliminary Report on Patentability for International Patent Application No. PCT/US2020/038944 dated Jan. 20, 2022, 8 pages.
(Continued)

*Primary Examiner* — Joshua Lee
(74) *Attorney, Agent, or Firm* — NK Patent Law

(57) ABSTRACT

Nasal respiratory assembly comprises a pair of sheets. Each sheet defines an opening sized and shaped to fit over the nostril of a patient, with a ferromagnetic ring positioned at an underside of the sheet, with an upper side of the sheet configured for sealable engagement with the nostril. A pair of posts is provided, each post including a magnetic ring positioned at a first end and a receptacle positioned at a second end, the magnetic ring removably attachable to the ferromagnetic ring. A connector is also provided, the connector including a pair of channel openings at a post end, each channel opening sized and shaped to cooperate with one of the post receptacles to form a substantially airtight connection therewith, and an inlet at a vent end that is fluid communication with a flexible tubing connected to a fluid source.

14 Claims, 27 Drawing Sheets

Related U.S. Application Data

(60) Provisional application No. 62/872,776, filed on Jul. 11, 2019.

(51) Int. Cl.
*A61M 16/08* (2006.01)
*A61M 16/12* (2006.01)
*A61M 16/16* (2006.01)

(52) U.S. Cl.
CPC ............ *A61M 16/12* (2013.01); *A61M 16/16* (2013.01); *A61M 2205/0272* (2013.01)

(58) Field of Classification Search
CPC .. A61M 16/0825; A61M 16/12; A61M 16/16; A61M 2016/0027; A61M 2202/0208; A61M 2202/0216; A61M 2202/0225; A61M 2205/0216; A61M 2205/0238; A61M 2205/0272; A61M 2205/6045; A61M 2210/0618
See application file for complete search history.

(56) References Cited

U.S. PATENT DOCUMENTS

| | | | | |
|---|---|---|---|---|
| 9,149,595 | B2* | 10/2015 | Heatherington | .. A61M 16/0825 |
| 9,517,317 | B2 | 12/2016 | McAuley et al. | |
| 10,206,571 | B2* | 2/2019 | Ewers | ............... A61M 16/0069 |
| 10,265,493 | B2* | 4/2019 | Heatherington | .. A61M 16/0688 |
| 10,905,842 | B2* | 2/2021 | Heatherington | .. A61M 16/0605 |
| 2007/0163600 | A1 | 7/2007 | Hoffman | |
| 2013/0131534 | A1* | 5/2013 | Heatherington | .. A61M 16/0493 128/205.25 |
| 2013/0263858 | A1 | 10/2013 | Ho et al. | |
| 2015/0075530 | A1 | 3/2015 | Collazo et al. | |
| 2015/0250972 | A1 | 9/2015 | Haibach et al. | |
| 2016/0022947 | A1* | 1/2016 | Heatherington | .. A61M 16/0825 128/205.25 |
| 2017/0368291 | A1* | 12/2017 | Heatherington | .. A61M 16/0493 |
| 2018/0296785 | A1* | 10/2018 | Heatherington | .. A61M 16/0605 |
| 2019/0175863 | A1 | 6/2019 | Hocking et al. | |

FOREIGN PATENT DOCUMENTS

| | | |
|---|---|---|
| WO | 2020242737 A1 | 12/2020 |
| WO | 2021194734 A1 | 9/2021 |

OTHER PUBLICATIONS

PCT, International Search Report and Written Opinion in International application No. PCT/US20/38944 dated Sep. 24, 2020.

EPO, Extended European Search Report for corresponding European Patent Application No. 20837534.5, dated Jun. 27, 2023, 9 pages.

JPO, Chinese Action for corresponding Japanese Patent Application No. 2022-502104, dated Jan. 9, 2024, 9 pages (including English translation).

* cited by examiner

RESPIRATORY ASSEMBLY AND METHODS OF USING THE SAME

CROSS-REFERENCE TO RELATED APPLICATIONS

This application is a continuation of International Application No. PCT/US2020/038944 filed Jun. 22, 2020, which claims priority to U.S. Provisional Patent Application 62/872,776 filed on Jul. 11, 2019, the contents of which is hereby incorporated by reference in its entirety.

TECHNICAL FIELD

The presently disclosed subject matter relates to a respiratory assembly, and particularly to a respiratory assembly having a nostril engaging portion for providing sealable engagement with nostrils.

BACKGROUND

Facial masks and nasal cannula are typically used for treating individuals with sleeping and breathing disorders. High flow delivery of respirator gas can be delivered to an individual using a nasal cannula and/or a facial mask. Continuous positive airway pressure (CPAP) masks can deliver a treatment fluid such as ambient air or oxygen-enriched air to a patient under a predetermined or desired pressure setting.

Masks and cannula that currently exist in the market are typically bulky, making them less aesthetically pleasing less and ergonomically effective. Further, conventional masks and cannula must provide sealable engagement with the patient's skin, leaving unsightly wear marks that require significant amounts of time to dissipate. The depressions or marks result from both the ridges of the mask enveloping the mouth and/or the nostril and from the straps or connections positioned about the individual's head. Due to the bulky nature of conventional masks and cannula, the ability of the wearer to move his/her head during sleep is constrained. For example, when the wearer of a conventional mask lies on her side during sleep, the wearer's pillow can contact and dislodge the mask, thereby evacuating the pressure within the mask assembly. As a result, the wearer wakes up or otherwise does not receive treatment gases under the ideal pressure.

Accordingly, there is a need for an improved respiratory assembly that addresses the disadvantages associated with conventional masks.

SUMMARY

This summary is provided to introduce in a simplified form concepts that are further described in the following detailed descriptions. This summary is not intended to identify key features or essential features of the claimed subject matter, nor is it to be construed as limiting the scope of the claimed subject matter.

Disclosed herein is a nasal respiratory assembly. According to various embodiments, the nasal respiratory assembly comprises a pair of sheets, each sheet defining an opening sized and shaped to fit over the nostril of a patient, with a ferromagnetic dome-shaped ring positioned at an underside of the sheet and circumferentially aligned with the opening, with an upper side of the sheet configured for sealable engagement with the nostril. The nasal respiratory assembly further comprises a pair of posts, each post including a magnetic ring positioned at a first end and a receptacle positioned at a second end with a passageway extending from the first to the second ends, the magnetic ring removably attachable to the dome-shaped ring. The nasal respiratory assembly furthermore comprises a connector with a pair of channel openings at a post end, each channel opening sized and shaped to cooperate with one of the post receptacles to form a substantially airtight connection therewith, and an inlet at a vent end that is fluid communication with a flexible tubing connected to a fluid source.

According to one or more embodiments, each receptacle is configured to be inserted into a channel opening.

According to one or more embodiments, each receptacle includes one or more releases that can be pivoted to maintain or release the post within a channel opening.

The assembly of claim 1, further comprising a vent connecting the inlet at the vent end of the connector to the flexible tubing connected to the fluid source.

According to one or more embodiments, the fluid source is selected from a high flow generator, a continuous positive airway pressure (CPAP) machine, a fluid tank, or a humidifier.

According to one or more embodiments, the fluid is selected from a gas, a mixture of gases, or a gas with a medication.

According to one or more embodiments, the flexible tubing has an inner diameter of about 2-4 mm.

According to one or more embodiments, an upper surface of the post is angled.

According to one or more embodiments, the angle is about 0-45 degrees.

Disclosed herein is a nasal respiratory assembly. The nasal respiratory assembly comprises a pair of sheets, each sheet defining an opening sized and shaped to fit over the nostril of a patient, with a ferromagnetic ring positioned at an underside of the sheet and circumferentially aligned with the opening, with an upper side of the sheet configured for sealable engagement with the nostril. The nasal respiratory assembly further comprises a pair of posts, each post including a magnetic ring positioned at a first end and a ball shaped receptacle positioned at a second end with a passageway extending from the first to the second ends, the magnetic ring removably attachable to the ferromagnetic ring. The nasal respiratory assembly furthermore comprises a connector with a pair of socket openings at a post end, each socket opening sized and shaped to receive the ball shaped receptacle in a ball and socket arrangement to form a substantially airtight connection therewith, and an inlet at a vent end that is fluid communication with a flexible tubing connected to a fluid source.

According to one or more embodiments, each ball shaped receptacle is configured to be inserted into a socket opening.

According to one or more embodiments, the assembly further comprises a vent connecting the inlet at the vent end of the connector to the flexible tubing connected to the fluid source.

According to one or more embodiments, the fluid source is selected from a high flow generator, a continuous positive airway pressure (CPAP) machine, a fluid tank, or a humidifier.

According to one or more embodiments, the fluid is selected from a gas, a mixture of gases, or a gas with a medication.

According to one or more embodiments, the flexible tubing has an inner diameter of about 2-4 mm.

According to one or more embodiments, wherein an upper surface of the post is angled.

According to one or more embodiments, wherein the angle is about 0-45 degrees.

Disclosed herein is a nasal respiratory assembly. The nasal respiratory assembly comprises a pair of sheets, each sheet defining an opening sized and shaped to fit over the nostril of a patient, with a ferromagnetic ring positioned at an underside of the sheet and circumferentially aligned with the opening, with an upper side of the sheet configured for sealable engagement with the nostril. The nasal respiratory assembly further comprises a pair of posts, each post including a magnetic ring positioned at a first end and a receptacle positioned at a second end with a passageway extending from the first to the second ends, the magnetic ring removably attachable to the ferromagnetic ring. The nasal respiratory assembly furthermore comprises a connector with a pair of channel openings at a post end, each channel opening sized and shaped to cooperate with one of the post receptacles to form a substantially airtight connection therewith, and an inlet at a vent end that is fluid communication with a flexible tubing connected to a fluid source.

According to one or more embodiments, wherein an upper surface of the magnetic ring is angled.

According to one or more embodiments, wherein the angle is about 0-45 degrees.

Disclosed herein is a nasal respiratory assembly. The nasal respiratory assembly comprises a pair of sheets, each sheet defining an opening sized and shaped to fit over the nostril of a patient, with a ferromagnetic ring positioned at an underside of the sheet and circumferentially aligned with the opening, with an upper side of the sheet configured for sealable engagement with the nostril. The nasal respiratory assembly further comprises a connector including a pair of slip rings at a sheet end, each slip ring including a magnetic ring defining a channel opening, the magnetic ring configured to pivotably tilt about the slip ring, each magnetic ring sized and shaped to removably attachable to one of the ferromagnetic rings to form a substantially airtight connection therewith, and an inlet at a vent end that is fluid communication with a flexible tubing connected to a fluid source, wherein the channel opening has a round, oblong, oval or tear drop shape.

According to one or more embodiments, an opening of the ferromagnetic ring has a round, oblong, oval or tear drop shape, wherein the shape of the opening of the ferromagnetic ring compliments or matches the shape of the channel opening of the magnetic ring.

According to one or more embodiments, the nasal respiratory assembly further comprises a hollow elbow connecting the inlet at the vent end of the connector to the flexible tubing connected to the fluid source.

According to one or more embodiments, the nasal respiratory assembly further comprises a swivel coupling connecting the hollow elbow to the flexible tubing.

BRIEF DESCRIPTION OF THE DRAWINGS

The foregoing, as well as the following Detailed Description of preferred embodiments, is better understood when read in conjunction with the appended drawings. For the purposes of illustration, there is shown in the drawings exemplary embodiments; however, the presently disclosed subject matter is not limited to the specific methods and instrumentalities disclosed.

The embodiments illustrated, described, and discussed herein are illustrative of the present invention. As these embodiments of the present invention are described with reference to illustrations, various modifications or adaptations of the methods and or specific structures described may become apparent to those skilled in the art. It will be appreciated that modifications and variations are covered by the above teachings and within the scope of the appended claims without departing from the spirit and intended scope thereof. All such modifications, adaptations, or variations that rely upon the teachings of the present invention, and through which these teachings have advanced the art, are considered to be within the spirit and scope of the present invention. Hence, these descriptions and drawings should not be considered in a limiting sense, as it is understood that the present invention is in no way limited to only the embodiments illustrated.

DETAILED DESCRIPTION

Figure 1:
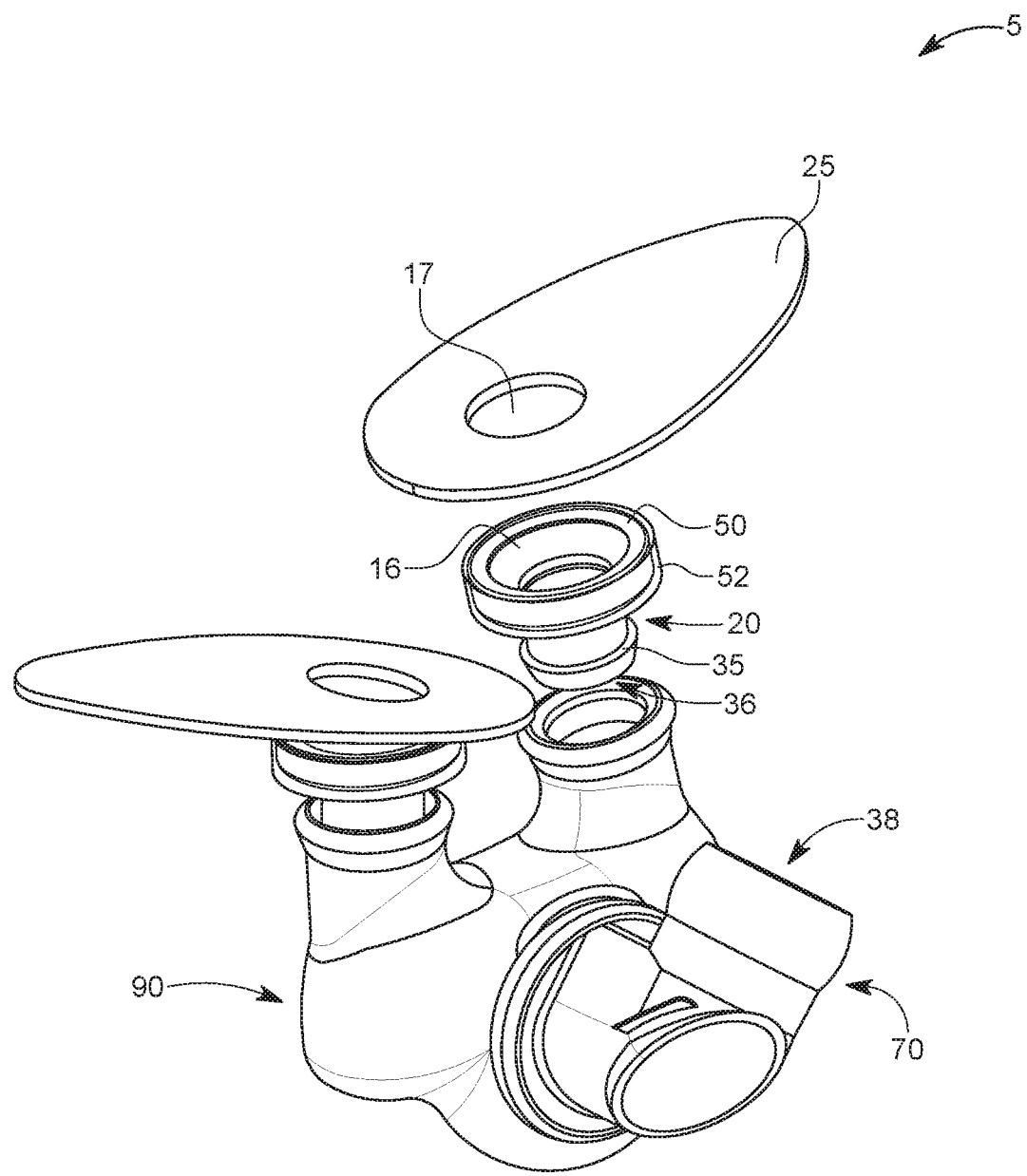
FIGS. 1 to 4 are perspective views of a nasal respiratory assembly in accordance with some embodiments of the presently disclosed subject matter.
Figure 2:
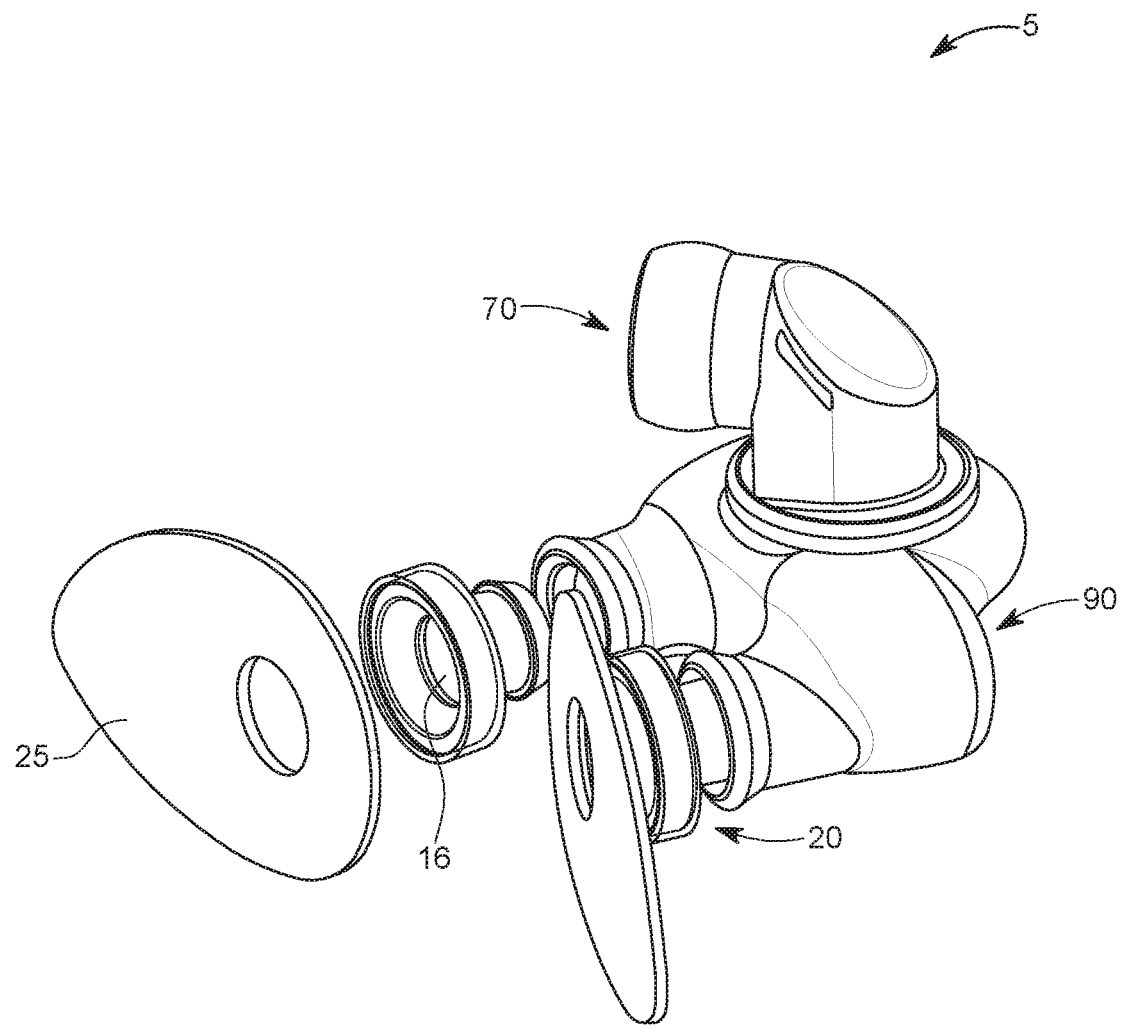

Below, the technical solutions in the examples of the present invention are depicted clearly and comprehensively with reference to the figures according to the examples of the present invention. Obviously, the examples depicted here are merely some examples, but not all examples of the present invention. In general, the components in the examples of the present invention depicted and shown in the figures herein can be arranged and designed according to different configurations. Thus, detailed description of the examples of the present invention provided in the figures below are not intended to limit the scope of the present invention as claimed, but merely represent selected examples of the present invention. On the basis of the examples of the present invention, all of other examples that could be obtained by a person skilled in the art without using inventive efforts will fall within the scope of protection of the present invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

These and other changes can be made to the disclosure in light of the Detailed Description. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features, or aspects of the disclosure with which that terminology is associated. In general, the terms used in the following claims should not be construed to limit the disclosure to the specific embodiments disclosed in the specification, unless the above Detailed Description of The Embodiments section explicitly defines such terms. Accordingly, the actual scope of the disclosure encompasses not only the disclosed embodiments, but also all equivalent ways of practicing or implementing the disclosure under the claims.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example, reference to "a device" can include a plurality of such devices, and so forth.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments +/−20%, in some embodiments +/−10%, in some embodiments +/−5%, in some embodiments +/−1%, in some embodiments +/−0.5%, and in some embodiments +/−0.1%, from the specified amount, as such variations are appropriate in the disclosed packages and methods.

Embodiments of the presently disclosed subject matter are directed to a nasal respiratory assembly. FIGS. 1 to 11 illustrate a nasal respiratory assembly such as nasal respiratory assembly 5 capable of being installed upon a patient according to one or more embodiments of the presently disclosed subject matter. As shown, the nasal respiratory assembly includes sheets 25 that are configured to engage the nares (i.e., nostrils) of the patient. The nasal respiratory assembly also includes socket magnet posts such as posts 20. One end of each post 20 is configured to removably attach to a ferromagnetic dome-shaped ring 62 on sheet 25 through the presence of a magnetic field; the other end of each post 20 is configured to engage an opening of nasal connector 90. In various embodiments, each post 20 can represent a socket magnet post. In one embodiment, ferromagnetic dome-shaped ring 62 can be a permanent magnet.

Nasal respiratory assembly 5 accordingly includes a pair of sheets 25, each sheet defining an opening 17 sized and shaped to fit over the nostril of a patient, with a ferromagnetic dome-shaped ring 62 positioned at an underside of the sheet and circumferentially aligned with the opening, with an upper side of the sheet configured for sealable engagement with the nostril.

Nasal respiratory assembly 5 includes a pair of posts 20, each post 20 including a magnet 50 (e.g. in the form of a magnetic ring as shown in FIG. 1) positioned at a first end and a receptacle 35 positioned at a second end with a passageway extending from the first to the second ends. Each magnet 50 defines an opening. The magnet 50 removably attaches to the ferromagnetic dome-shaped ring 62 at exit end 16. In one embodiment, magnet 50 is configured to pivotably move or rotate about the surface of ferromagnetic dome-shaped ring 62 in a ball and socket arrangement while continuing to maintain a substantially airtight connection at the interface between magnetic 50 and ferromagnetic dome-shaped ring 62. The ferromagnetic dome-shaped ring 62 can advantageously prevent or reduce the possibility of the nasal connector 90 inadvertently getting dislodged when the wearer of nasal respiratory assembly 5 moves the head—either while awake or while asleep—to thereby allow for the continued supply of treatment gases to a patient's nare under ideal pressure. In at least one embodiment, ferromagnetic dome-shape ring 62 can permit magnet 50 to pivotably move or rotate about the surface of ferromagnetic dome-shaped ring 62 in a ball and socket arrangement while continuing to maintain a substantially airtight connection therewith when the face of a patient wearing nasal respiratory assembly 5 is moved in a sudden jerky movement. In at least one embodiment, the ferromagnetic dome-shape ring 62 can permit magnet 50 to pivotably move or rotate about the surface of ferromagnetic dome-shaped ring 62 in a ball and socket arrangement while continuing to maintain a substantially airtight connection therewith when the wearer's pillow contacts or applies a shearing force against a portion of the nasal respiratory assembly 5 or against a tubing supplying fluid to the nasal respiratory assembly 5.

Nasal connector 90 of nasal respiratory assembly 5 includes a pair of channel openings 15, each channel opening 15 sized and shaped to cooperate with one of the receptacles 35 to form a substantially airtight connection therewith such that channel 36 of post 20 is aligned with channel opening 15 of nasal connector 90, and an inlet such as vent coupling 54 at a vent end that is configured for fluid communication with a flexible tubing connected to a fluid source. In one embodiment, a vent such as vent 70 is located between vent coupling 54 and the flexible tubing. Vent 70 includes vent receptacle 98 sized and shaped to cooperate with vent coupling 54 to form a substantially airtight connection therewith, and inlet 38 sized and shaped to cooperate with the flexible tubing such as tubing 10 shown in FIG. 21 to form a substantially airtight connection therewith.

Figure 11:
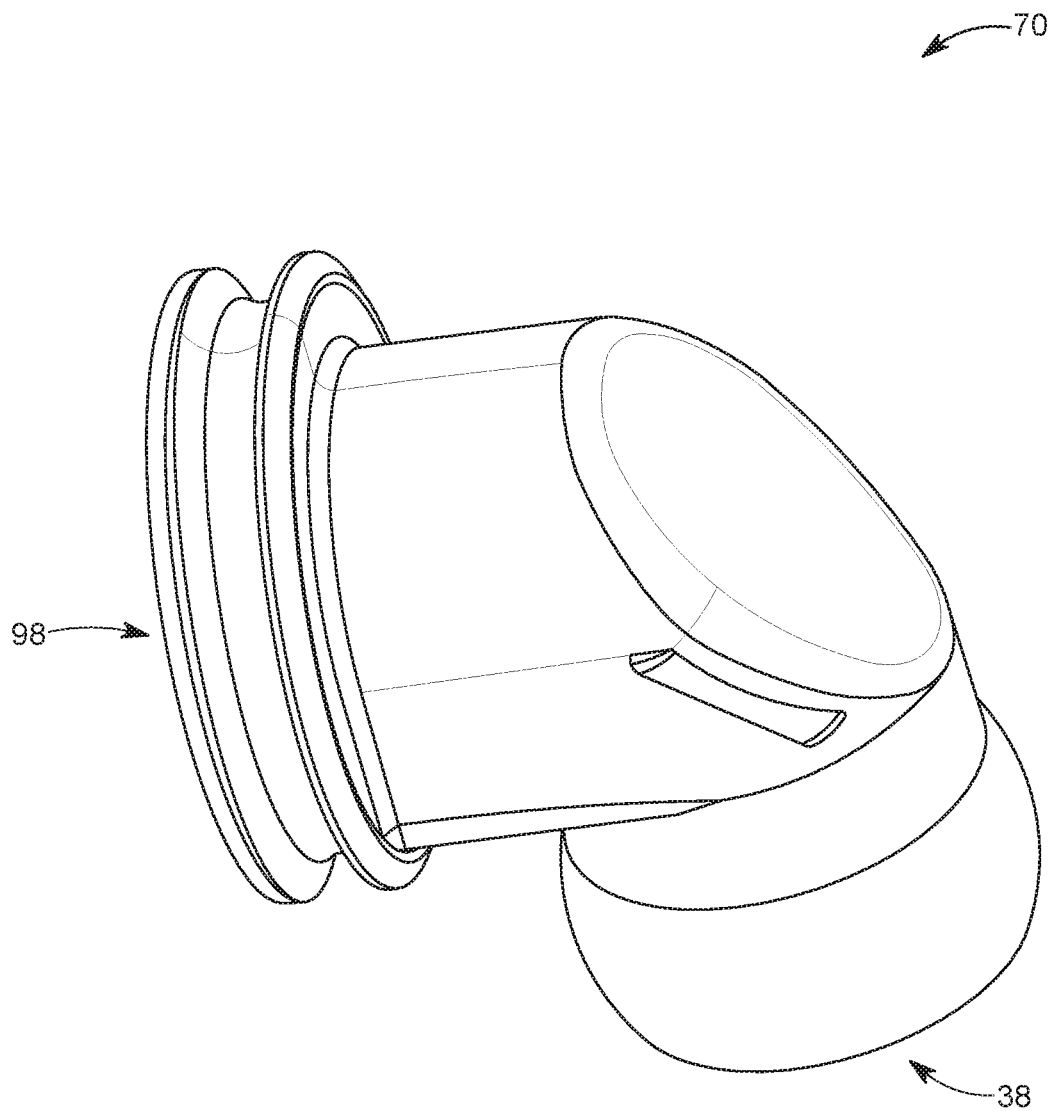
FIG. 11 is a side perspective view of a vent that can be used with the disclosed assembly in some embodiments.
Figure 12:
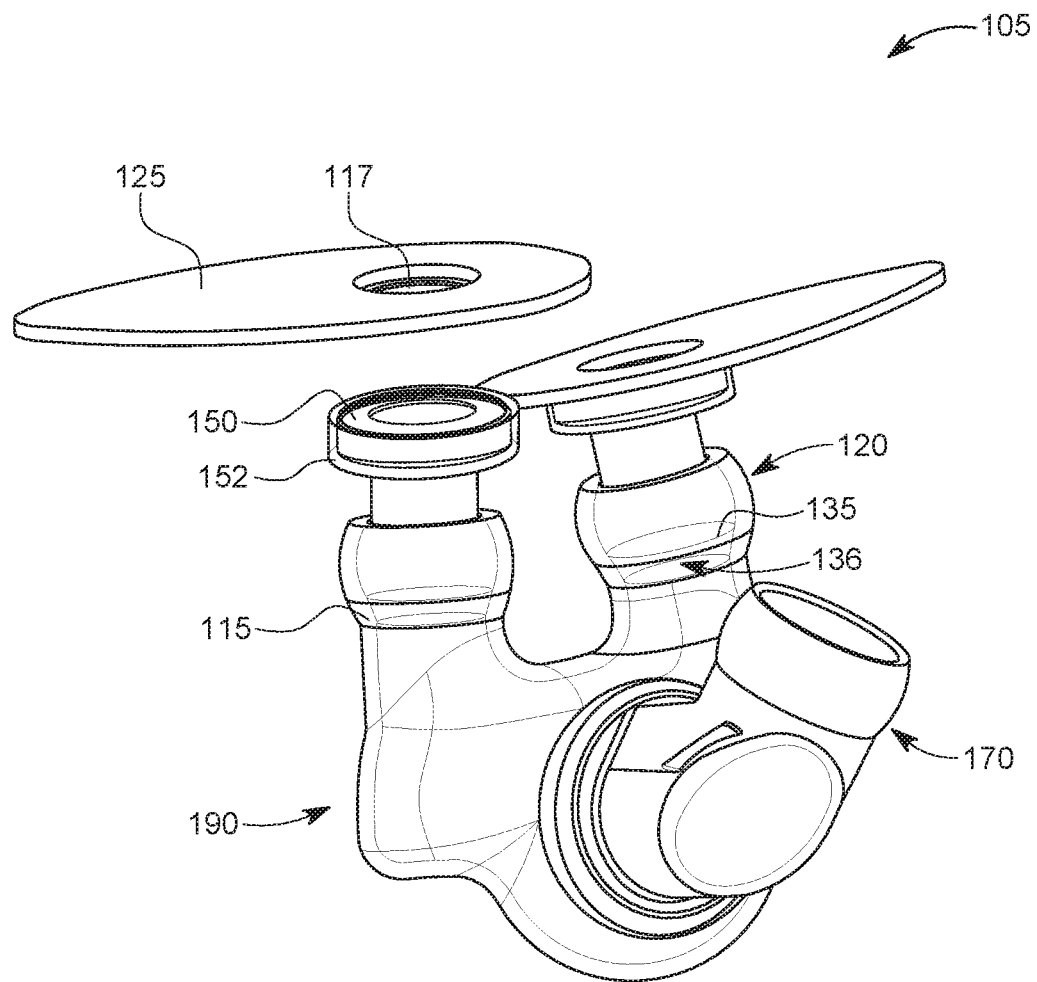
FIGS. 12 to 14 are perspective views of a nasal respiratory assembly in accordance with some embodiments of the presently disclosed subject matter.
Figure 13:
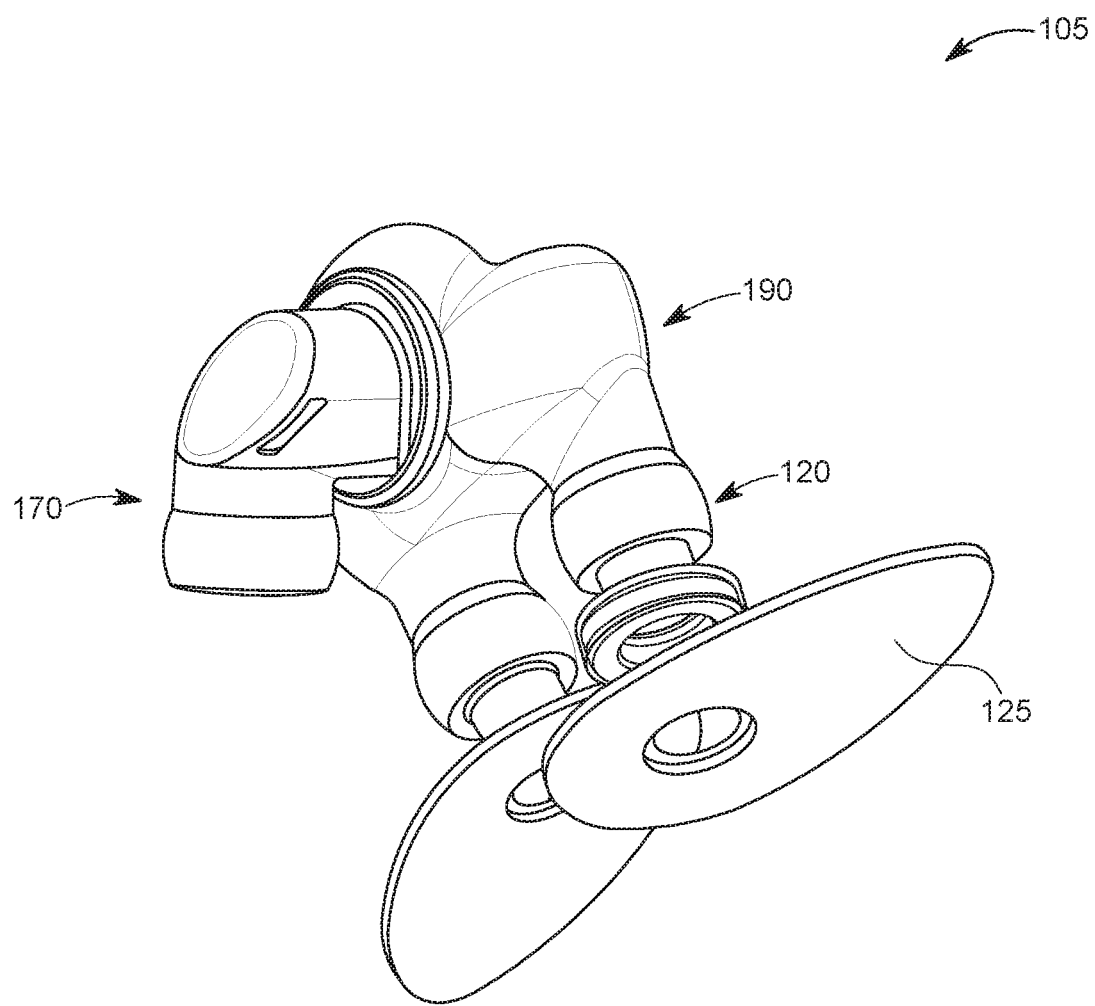
Figure 14:
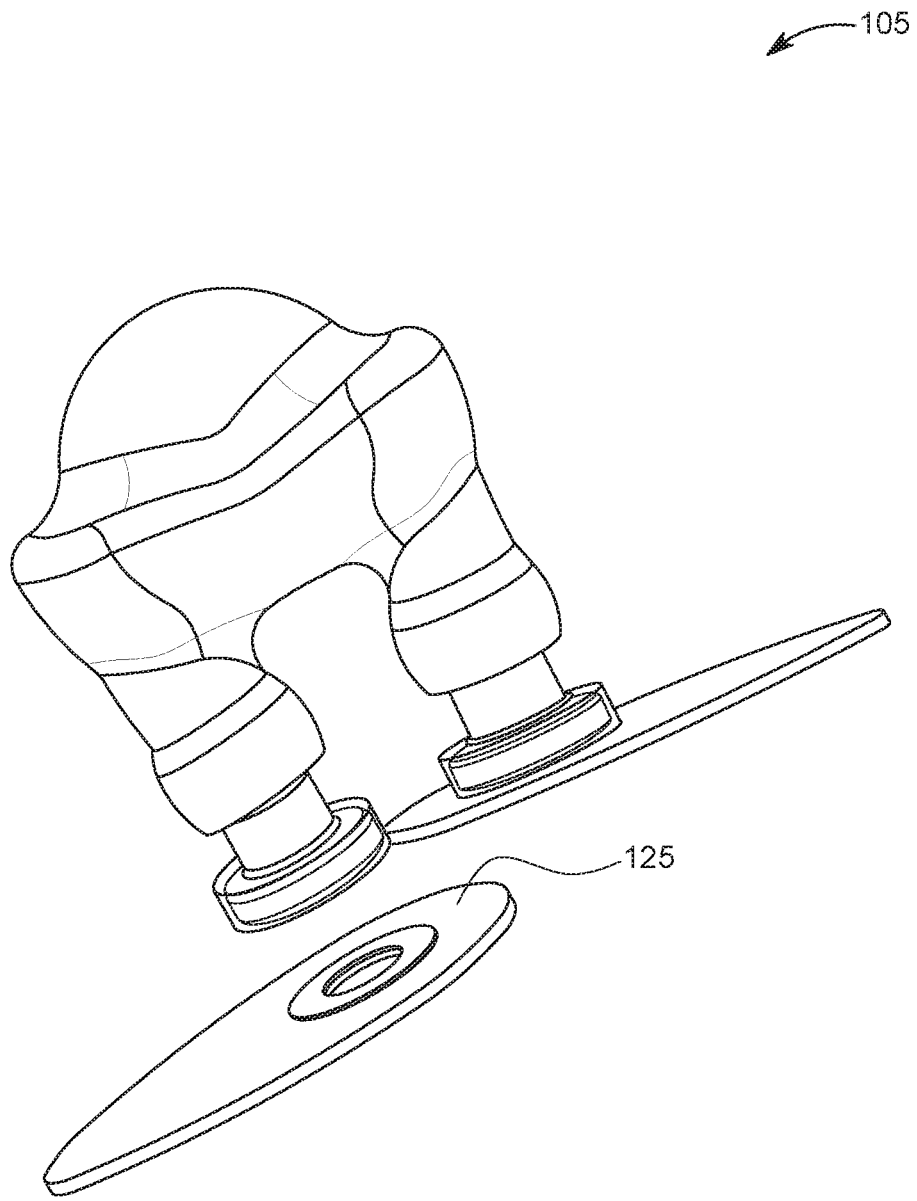
Figure 21:
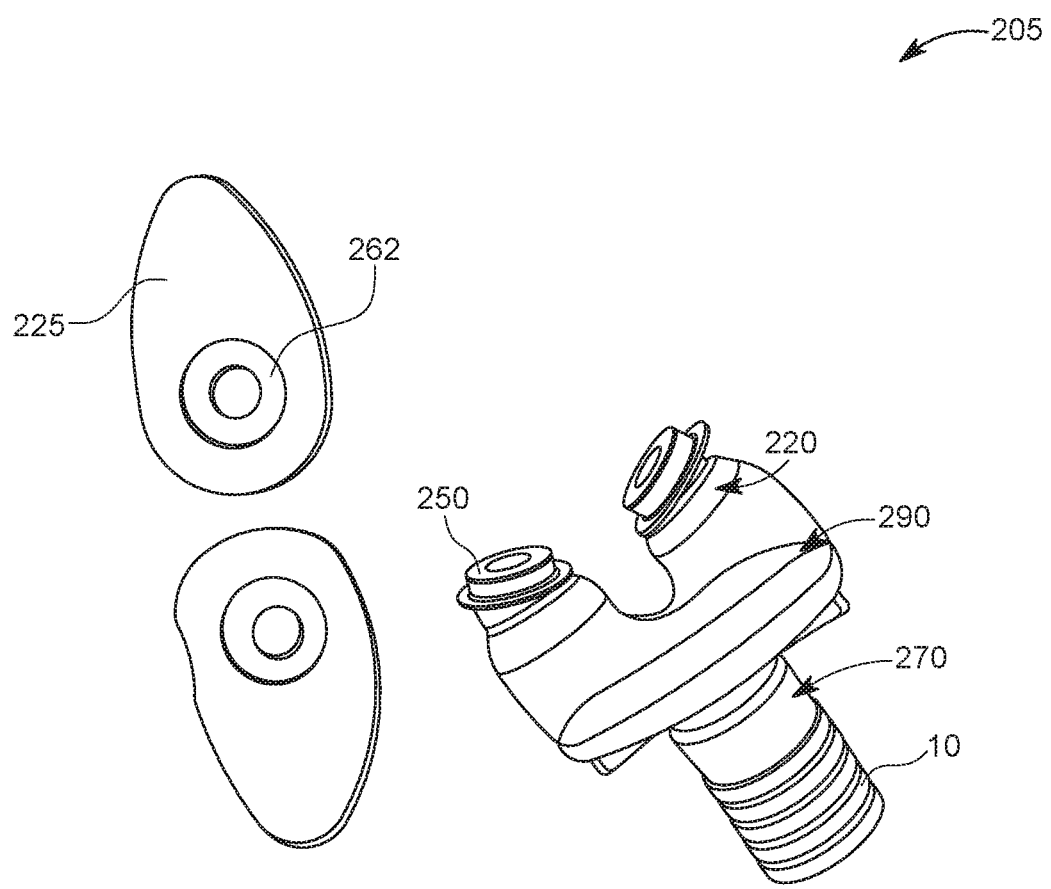

Nasal respiratory assembly 5 accordingly comprises at least one vent 70 for receiving treatment gases to the nasal cavity of a patient. As shown in FIG. 11, one end of vent 70 has an inlet 38 configured for connecting to a fluid source (not shown) via a fluid tubing such tubing 10 shown in FIG. 21 that provides the respiratory gas, while vent receptacle 98 located at the other end of vent 70 engages vent coupling 54 of nasal connector 90. Accordingly, nasal respiratory assembly 5 can include one or more vents 70 positioned proximal to where fluid flow occurs. It should be appreciated that vent 70 can be positioned at any desired location and its location is not limited to the locations illustrated herein. In some embodiments, vent 70 can comprise a socket including an adaptor. The adaptor can be constructed in any desired shape to allow for a substantially airtight connection with tubing 10 (tubing 10 is shown in FIG. 21). In some embodiments, tubing 10 represents a flexible tubing. In some embodiments, the outer diameter of the adaptor is greater than the inner diameter of tubing 10. In this way, the adaptor is held within the tubing for a desired amount of time, and the tubing cannot be accidentally un-lodged by the patient or wearer, such as during sleep. The adaptor can be releasably connected to tubing 10 using any known mechanism.

In some embodiments, the fluid source can be a high flow generator, a continuous positive airway pressure (CPAP) machine, a fluid tank, a humidifier, or any other fluid source known or used in the art. The term "fluid" as used herein refers to any gas, mixture of gases, or gas with medication (such as an aerosol medication) suitable for delivery to the airway of a human. A flexible tubing such as tubing 10 as shown in FIG. 21, for example, can couple with inlet 38 to supply the fluid from the fluid source. Tubing 10 can include any known flexible tubing. The term "tubing" as used herein refers to any conduit, a delivery conduit, a tube, pipe, passage, or channel through which fluid flows. The term "flexible" as used herein refers to any tubing that is able to flex or bend and that is compliant and will readily conform to the general shape and contours of the human body. In some embodiments, tubing 10 can be constructed from medical grade materials, such as (but not limited to) polyurethane, polyvinyl chloride, polyamide, polyester, polyolefin, silicone, fluoropolymer, and combinations or copolymers thereof. Tubing 10 can be flexible, resilient, and hollow. In some embodiments, tubing 10 can have an inner diameter of between about 2-4 mm, although tubing with larger or smaller diameters can be used. For example, the inner diameter of tubing 10 can be increased or decreased to adjust for a particular wearer's preferences and/or needs. In some embodiments, during use, tubing 10 can be hooked over the ears of a patient and can be brought up under the chin during use.

As shown in FIG. 1, for example, posts 20 are configured as nasal prongs that extend towards and contact ferromagnetic dome-shaped rings 62 of sheets 25 by way of contact between ferromagnetic dome-shaped rings 62 and magnets 50. Sheets 25 are configured for attaching to the nostrils of a wearer such that fluid received at inlet 38 is delivered into the nostrils of the wearer via the respective opening 17 in sheets 25. Ferromagnetic dome-shaped ring 62 is made an integral component of sheet 25 such that the openings of ferromagnetic dome-shaped ring 62 is aligned with respecting openings 17 of sheets 25.

Figure 8:
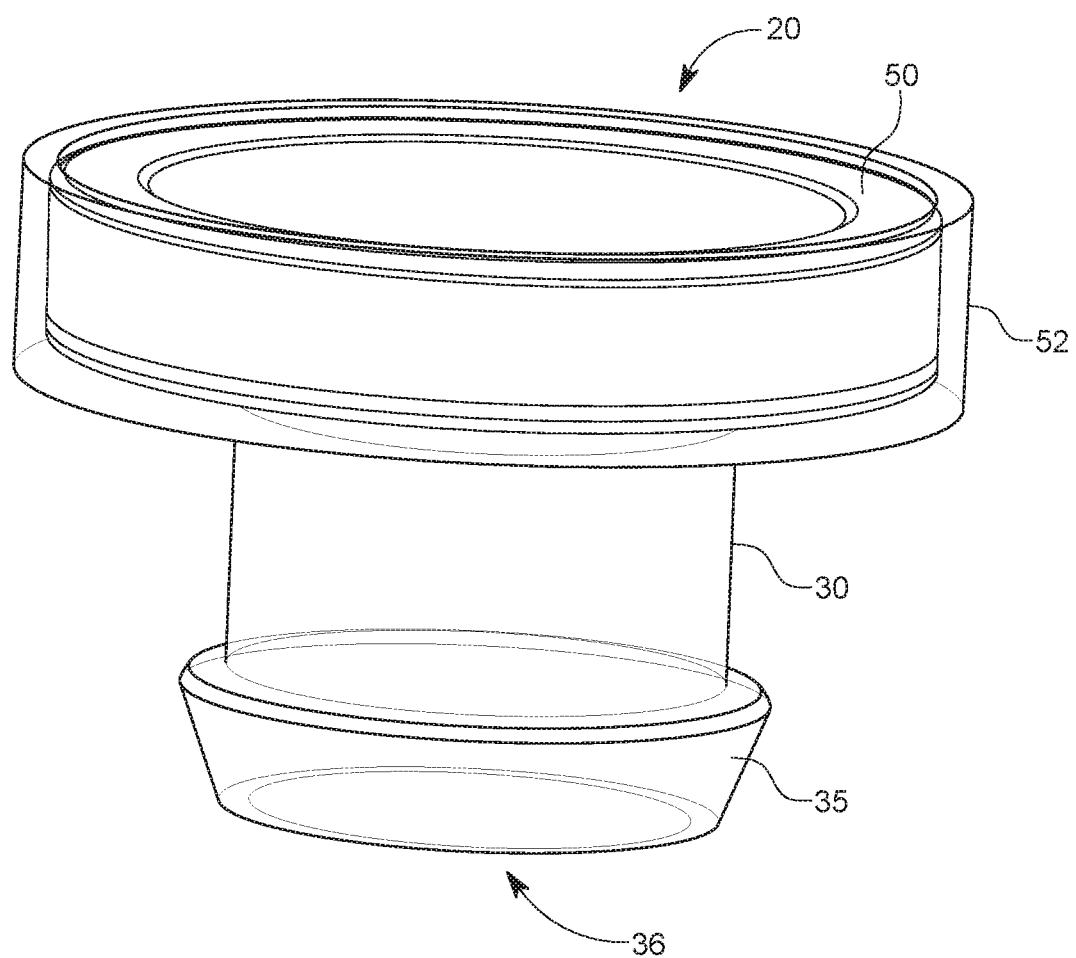
FIG. 8 is a side perspective view of a socket magnet post that can be used with the disclosed nasal respiratory assembly in some embodiments.
Figure 9:
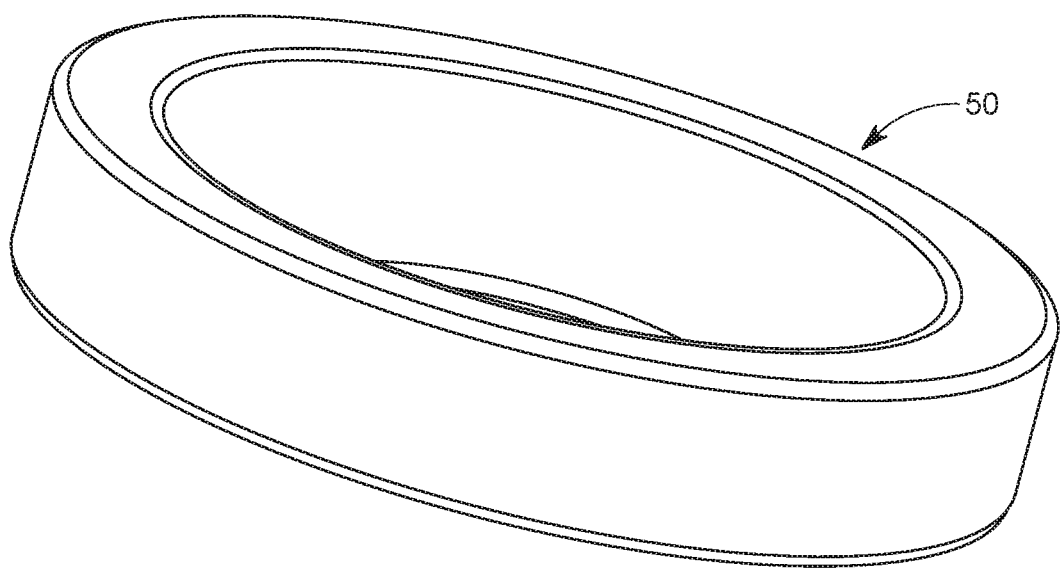
FIG. 9 is a side perspective view of a magnet that can be used with the disclosed nasal respiratory assembly in some embodiments.
Figure 10:
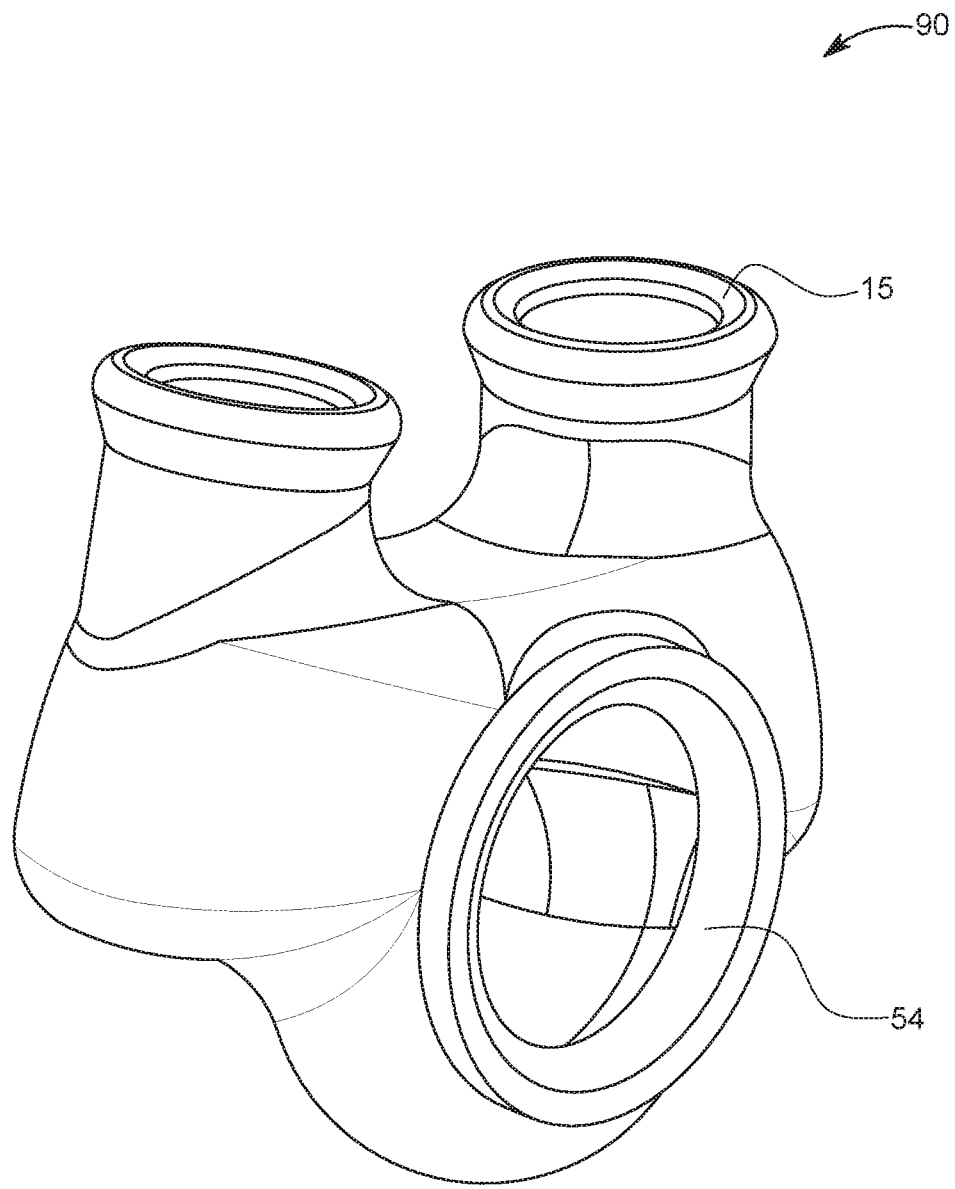
FIG. 10 is a side perspective view of a nasal connector that can be used with the disclosed nasal respiratory assembly in some embodiments.

As shown in FIG. 8, an upper end of each post 20 includes a magnet socket 52 configured to house a magnet such as magnet 50. Post 20 further includes post body 30, a receptacle 35 and channel 36. In some embodiments, posts 20 are parallel or about parallel to each other. While magnet 50 is shown to be ring shaped, other shapes are possible without deviating from the spirit of the presently disclosed subject matter; similarly, ferromagnetic dome-shaped ring 62 may take other shapes such that any shape taken by ferromagnetic dome-shaped ring 62 compliments or matches the shape of magnet 50. In various embodiments, ferromagnetic dome-shaped ring 62 is made of a ferromagnetic material such that it is attracted by the magnetic field of magnet 50 so as to form a substantially airtight bond or attachment therewith.

Figure 3:
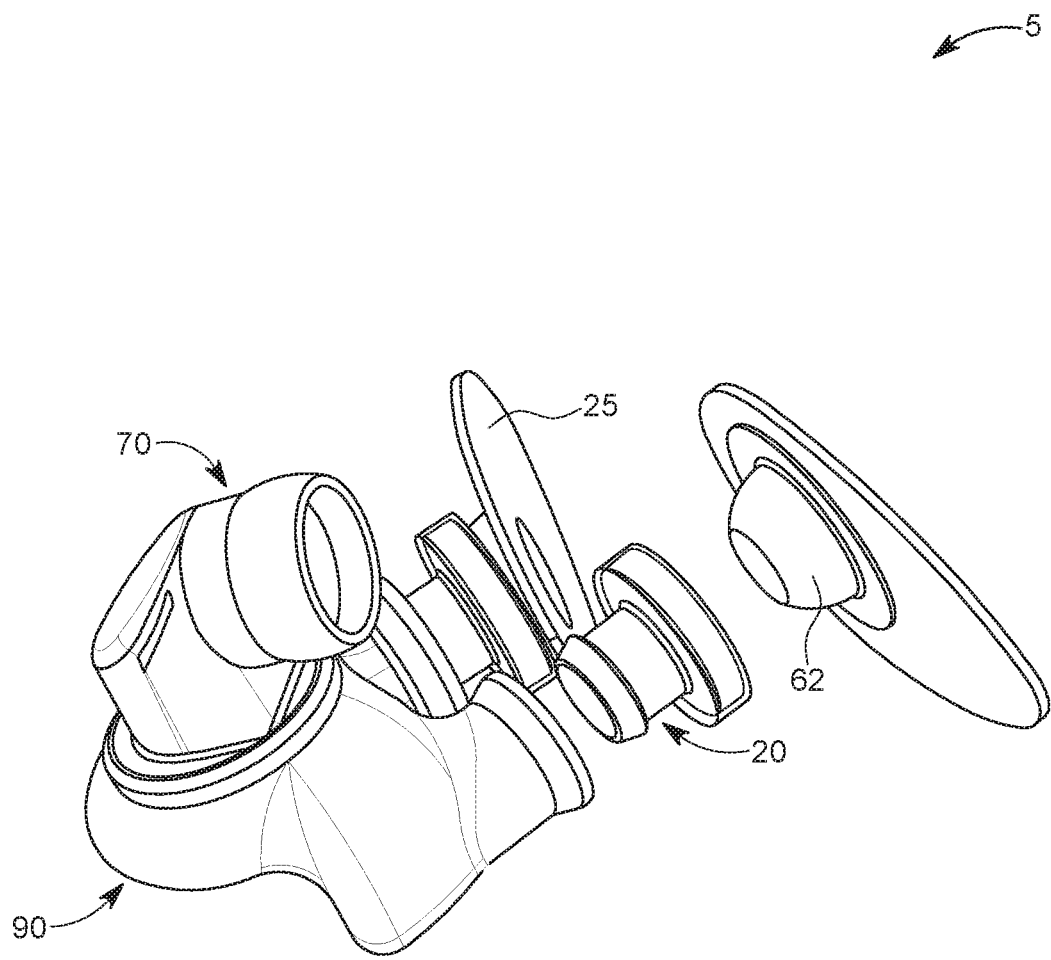
Figure 4:
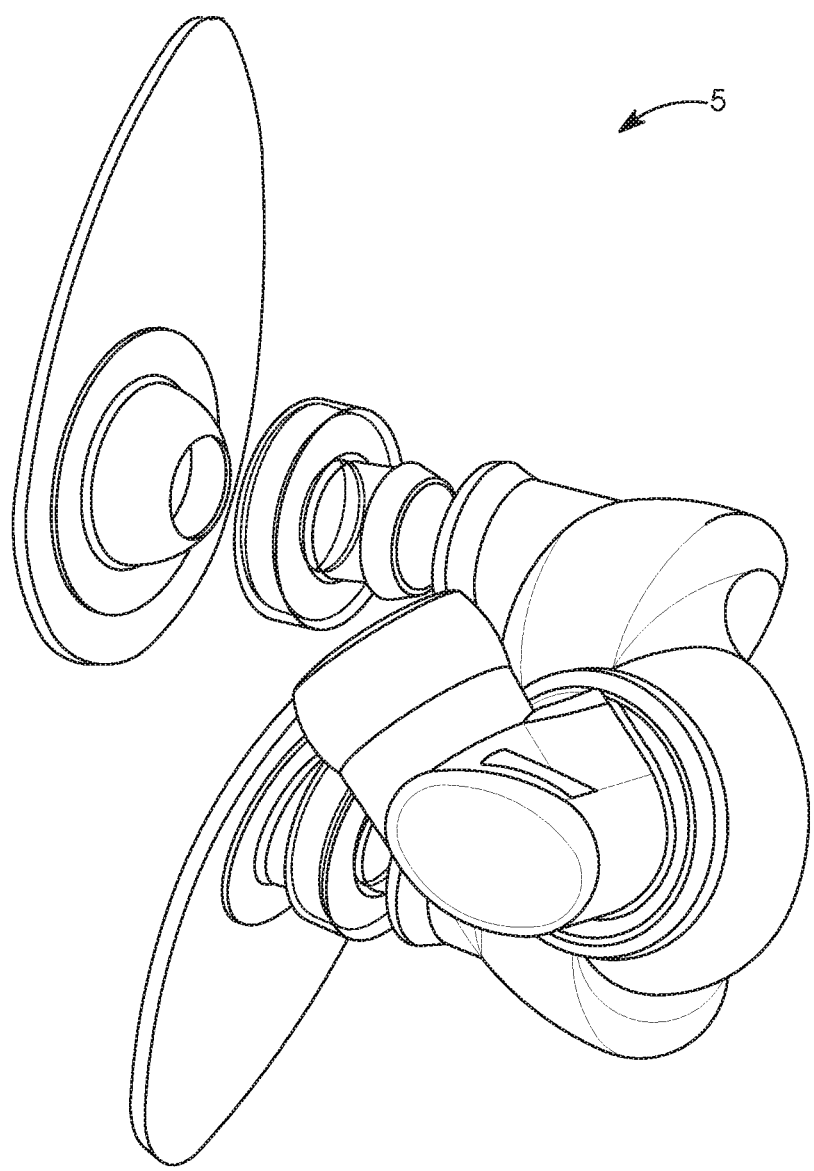
Figure 5:
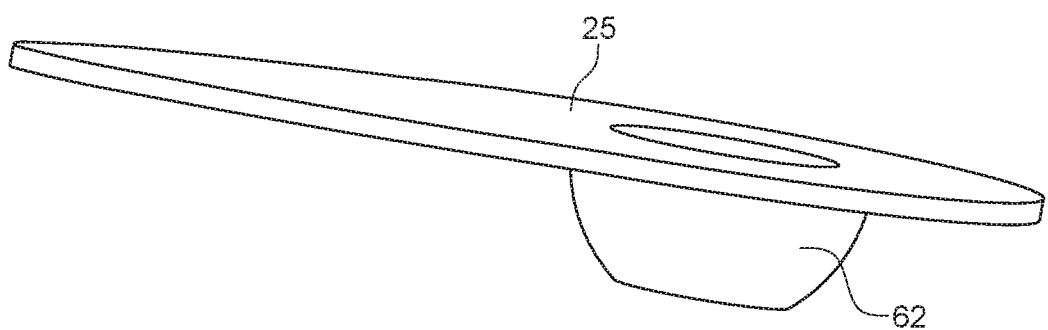
FIG. 5 is a side perspective view of a dome ring and a sheet that can be used with the disclosed nasal respiratory assembly in some embodiments.
Figure 6:
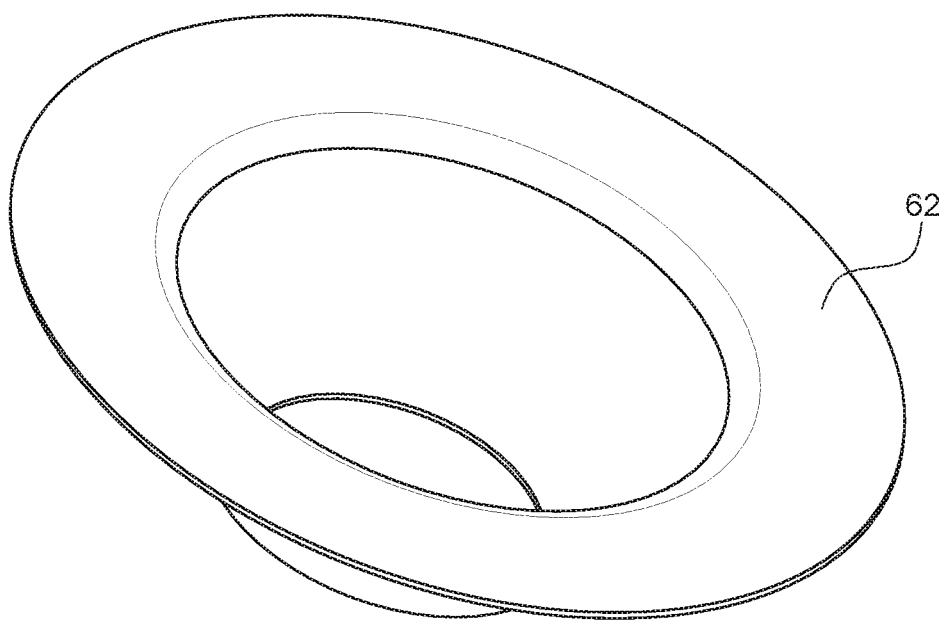
FIG. 6 is a top perspective view of a dome ring that can be used with the disclosed assembly in some embodiments.
Figure 7:
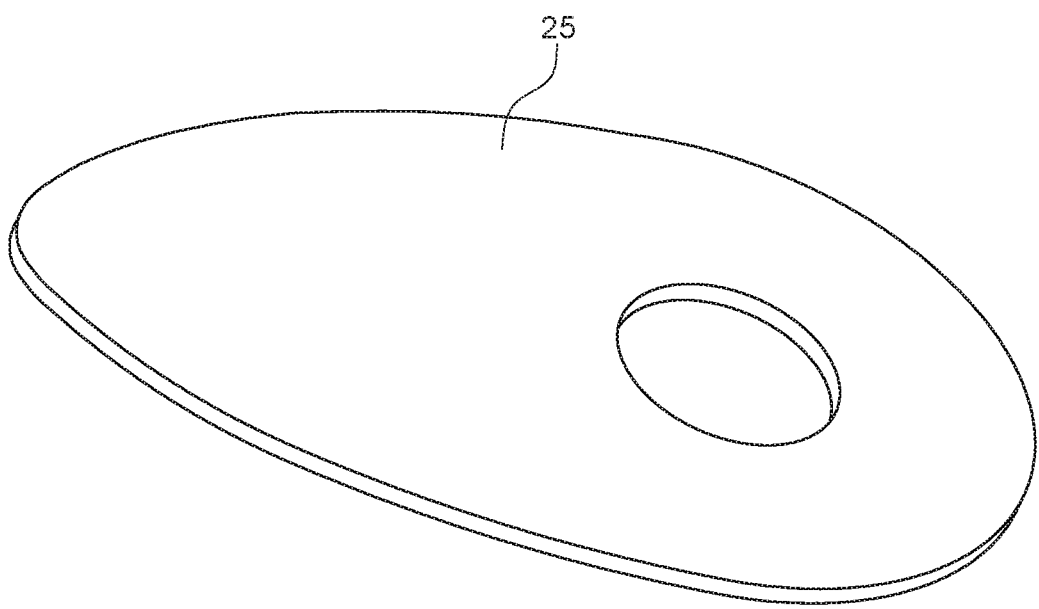
FIG. 7 is a top perspective view of a sheet that can be used with the disclosed assembly in some embodiments.

As shown in FIG. 3, an underside of sheet 25 includes the ferromagnetic dome-shaped ring 62 that cooperates with magnet 50 to provide a continuous conduit such that fluid received at inlet 38 is delivered into the nostrils of the wearer via the respective opening in sheet 25. When magnet 50 is detachably attached to ferromagnetic dome-shaped ring 62 of sheet 25, the upper end of each post 20, i.e., exit ends 16, are in fluid communication with the interior of the nostrils of the wearer, whereas the lower end of post 20 are in fluid communication with the interior of nasal connector 90 such that respiratory fluid flows from exit end 16 (i.e., upper post opening) of each post 20 and through opening 17 of each sheet 25 and into the interior of the nostrils of the wearer. Thus, each post comprises a unique pathway for conveying fluid from a fluid source to the nasal passage of the patient. The posts 20 can have various cross-sections, such as a circular, oval or rectangular in cross-section, with opening 17 having a shape that compliments or matches the cross-section of posts 20. Magnets 50 of posts 20 that are configured to engage with ferromagnetic dome-shaped rings 62 of sheets 25; sheets 25, in turn, are configured to engage the nostrils of the wearer or patient. The sheets can be configured for providing a flush, sealable engagement with the patient's nares. Each sheet 25 directly contacts the exterior of a patient's nostril or the skin surrounding the patient's nostril. The interior of post 20 includes a through opening in the form of channel 36 passing through the entire length thereof to allow fluid flow to the nasal cavity of the patient.

In some embodiments, each sheet 25 engages with or includes one or more flexible adhesive sheets (not separately illustrated) to provide sealable engagement with the patient's nostrils. Sheet 25 can be constructed from any known material, including (but not limited to) woven fabric, plastic, and/or latex. For example, in some embodiments, sheet 25 can be constructed from PVC, polyethylene, polyurethane, latex, or combinations thereof. In some embodiments, sheet 25 can be a foam medical tape, a surgical tape, and/or a hypoallergenic tape. As noted, the patient contacting surface of sheet 25 can include an adhesive. The adhesive can be any medically-safe adhesive known or used in the art. For example, the adhesive can be selected from one or more acrylates (such as methacrylate, alkyl acrylate, or epoxy diacrylate), acrylic acids, polyvinyl chloride, alkyl esters, or combinations thereof. In some embodiments, the adhesive is a pressure-sensitive adhesive such that sheet 25 can be adhered and removed from the patient's skin as desired. The adhesive can be selected such that it produces mild or no irritation to the skin when used daily. In some embodiments, the adhesive can be configured as a hydrocolloid tape and/or can include a polyurethane reactive layer that adheres more to the nostril as the patient's body temperature warms up the adhesive. Alternatively, in some embodiments, the adhesive can be directly applied to the patient's nostril or the nasal engaging portion to provide a removeable connection (e.g., no separate adhesive tape is used).

Magnet socket 52 is positioned about a first end of post 20. In some embodiments, magnet socket 52 (i.e., an upper surface of the post) can be angled in relation to post body 30 to allow for enhanced attachment to ferromagnetic dome-shaped ring 62 of sheet 25 for better positioning on the patient's nostrils (as illustrated, for example, in FIG. 20). In some embodiments, the angle can be between about 0-45 degrees, such as about 5, 10, 15, 20, 25, 30, 35, 40, or 45 degrees. For example, in some embodiments, a plane parallel to a circumference, a perimeter, or a largest dimension of the magnet socket 52 can be configured to make an angle of about 0-45 degrees with a plane that is perpendicular to a vertical axis passing through the center of a bottom portion of channel 36 that is closest to the channel openings of the connector. As another example, in some embodiments, a plane parallel to a circumference, a perimeter, or a largest dimension of the magnet socket 52 can be configured to make an angle of about 0-45 degrees with a major lateral plane that is perpendicular to a vertical axis passing through the center of the opening provided on vent 70. In some embodiments, the angle can be created by having a portion of the post body bulge outwards at an angle. In some embodiments, the angle can be created by modifying one or more components of nasal connector 90, including the area directly beneath channel opening 15. Alternatively, in some embodiments, post body 30 can remain substantially cylindrical, having a top portion cut at an angle. Post body 30 houses channel 36 within its interior to allow the flow of fluid to the nasal cavity of the patient. In some embodiments, post body 30 can have a circular, oval, or square cross-sectional shape. However, the shape of post body 30 is not limited and can be configured in any desired shape. Further, channel 36 can have any desired cross-sectional shape, such as square, triangular, circular, oval, and the like. Magnet socket 52, magnet 50 and opening 17 too can take various cross-sectional shapes. According to one or more embodiments, an upper surface of the magnetic ring is angled. In such embodiments, the magnetic ring can have different thicknesses in different regions of the magnetic ring.

In some embodiments, post 20 further includes receptacle 35 configured on a second post end for engaging channel opening 15 and/or a socket. In some embodiments, receptacle 35 can comprise a tapered ridge. However, the shape of the receptacle is not limited, and can be constructed to enable insertion of channel opening 15 and/or to enable connection with a socket provided at the end of channel opening 15. In some embodiments, receptacle 35 can be configured to selectively engage a receiving portion of channel opening 15. The engagement of receptacle 35 with channel opening 15 can be achieved using a number of different structural configurations. For example, receptacle 35 can be a circumferentially extending portion for selectively engaging a respective recess-receiving portion on channel opening 15. Alternatively, receptacle 35 can be a ball joint and the receiving portion on channel opening 15 can be a tube socket.

In some embodiments, post 20 can include one or more vents in communication with channel 36 to ensure that the patient's ability to breathe is not hampered, and to optionally further ensure excess fluid has an outlet. The vents can be sized and shaped in any desired configuration and can be positioned proximal to any of the regions where fluid flow occurs. Thus, the vents can be positioned on the flange, body, and/or connector of the post. The vents can vary in size and location such that manipulation of all exhaled fluids (e.g., $CO_2$) is controlled and titratable to alter the flow rate to a desired setting. In some embodiments, the vents can include polymeric fibers, membranes, and/or webs with an extremely small thickness (e.g., from nanoscale to microscale).

Post 20 can be constructed from any desired material. For example, the post can be constructed from rubber, silicone polymers, acrylate polymers, or combinations thereof. It should be appreciated that the materials used to construct post are not limited to the materials cited herein. Post 20 can be attached to the exterior portion of each patient nostril by affixing sheets 25 directly to the skin surrounding the nostril, and then attaching magnet 50 to ferromagnetic dome-shaped ring 62. In this arrangement, channel 36 is positioned in line with the nostril opening. In some embodiments, a further sheet comprising an adhesive can be used can be used to attach the sheet to the nostril. Thus, the adhesive side of the further sheet can be used to adhere sheet 25 to the skin of the patient. Post 20 along with sheet 25 can be configured for providing a flush, sealable engagement with the patient's nostril. After post 20 has been affixed to the exterior portion of each of the patient's nostrils, channel opening 15 of nasal connector 90 can be translated towards channel 36 at the second end of post 20. Open exit ends 16 (gas-flow end) of the post is in a substantially airtight attachments with ferromagnetic dome-shaped ring 62. Fluid flows from the tubing, through the interior of the nasal connector, exits the post via exit end 16 and flows into the patient's nasal passages.

In use, sheet 25 can be attached to the exterior portion of each nostril by affixing sheet 25 directly to the skin surrounding the nostril, as set forth in detail herein above. Post 20 in connected arrangement with a fluid source via tubing such as tubing 10 is then translated towards the sheet such that magnet 50 attaches to ferromagnetic dome-shaped ring 62 of sheet 25. When a user desires to uncouple the post and sheet, magnet 50 can be detached from ferromagnetic dome-shaped ring 62 by gently pulling one or more of the nasal connector, the tubing, the post, and the vent away from the nostrils such that ferromagnetic dome-shaped ring 62 of sheet 25 detaches from magnet 50. In one embodiment, ferromagnetic dome-shaped ring 62 is itself a permanent magnet (rather than ferromagnetic dome-shaped ring 62 being formed of a material that magnet 50 attracts). Ferromagnetic dome-shaped ring 62 itself being a permanent magnet can advantageously operate to improve the bond between ferromagnetic dome-shaped ring 62 and magnet 50 in one implementation.

The nasal respiratory assembly disclosed herein has a wide variety of applications. For example, in some embodiments, the nasal respiratory assembly can be used for high flow delivery of respirator gas via nasal respiratory assembly. In some embodiments, the air can be heated to near body temperature (e.g., about 37° C.) and/or humidified (e.g., about 100% relative humidity) to decrease airway moisture loss, airway cooling, nasal irritation, and the like. In high flow therapy, the source of oxygen is typically blended with compressed air, allowing the delivery of air, blends of air and oxygen from about 22% to about 99%, or delivery of 100% oxygen with the use of an oxygen blender. Advantageously, the disclosed nasal respiratory assembly can include tubing large enough to deliver flow rate of respiratory gas of up to about 50 liters per minute for adults. The nasal respiratory assembly and its components can also be configured to be small enough such as to allow fluid flow during exhalation and to further allow the escape of excess gas during inhalation. Beneficially, because the delivered flow rate can meet the inspiration flow rate, the delivered gases are not diluted by room air.

Alternatively, or in addition, the disclosed nasal respiratory assembly can be used with a continuous positive airway pressure (CPAP) machine. CPAP machines typically apply mild air pressure on a continuous basis to keep a patient's airway continuously open. As a result, CPAP machines used in conjunction with a patient's stent can advantageously cause the lungs' alveoli to open and thus recruit more of the lung's surface area for ventilation. CPAP machines are generally used for people with breathing problems, such as sleep apnea. Alternatively, CPAP machines can be used to treat pre-term infants whose lungs have not yet fully developed. In some embodiments, the disclosed nasal respiratory assembly can be used as a replacement for traditional CPAP masks.

The disclosed nasal respiratory assembly can further be used in pressure recording applications in clinical settings, such as to diagnose sleep apnea or other disorders. Particularly, sleep apnea can be diagnosed based on characteristic clinical features associated with episodes of cessation of breathing that define hypopnoeic and apnoeic events. The disclosed nasal respiratory assembly can be used to measure nasal pressure by measuring nasal pressure with nasal prongs connected to a pressure transducer.

The disclosed assembly can further be used with a fluid tank, a humidifier, or any other fluid source known or used in the art. Advantageously, the disclosed nasal respiratory assembly may eliminate over-the-ear soreness and lip soreness commonly found in traditional respiratory masks and cannula. In addition, the disclosed nasal respiratory assembly may enable better control of gases (e.g., oxygen) during fluid delivery applications. In some embodiments, the disclosed nasal respiratory assembly is strapless and maskless, thereby increasing using comfort. As a result, patients are more likely to follow doctor's orders and use the assembly. In addition, unsightly mask and strap skin indentations are eliminated. The disclosed nasal respiratory assembly is less likely to be dislodged inadvertently by the patient, such as during movement or when being pressed against a pillow.

In some embodiments, the disclosed nasal respiratory assembly can include a sanitizing enclosure that can be used to sanitize the reusable portions of the CPAP assembly in the form of the nasal respiratory assembly disclosed herein. The term "sanitizing" as used herein refers to the elimination of all or nearly all microbial forms. The sanitizing enclosure can include an activated oxygen and/or UV light generator that is used to clean and/or sanitize the reusable CPAP elements. For example, in some embodiments, the generator can generate activated oxygen to sanitize the contents of interior of the enclosure and the reusable CPAP system Activated oxygen (also known as $O_3$ or ozone) is a safe, naturally-occurring gas that has been shown to kill virtually all known forms of viruses in water and air. Particularly, activated oxygen has been shown to interfere with the metabolism of bacterium cells, likely through inhibiting and blocking the operation of the enzymatic control system. A sufficient amount of activated oxygen breaks through the cell membrane, leading to destruction of the bacteria. Activated oxygen destroys viruses by diffusing through the protein coat into the nucleic acid core, resulting in damage to the viral RNA. At higher concentrations, activated oxygen destroys the viral capsid by oxidation to affect the DNA or RNA structure. Activated oxygen has been shown to be effective in destroying dozens of harmful pathogens, including *E. coli*, influenza virus, Staphylococcus, *Streptococcus* bacteria, Stomatitis virus, and many more.

In some embodiments, the generator can produce activated oxygen in a concentration of about 10-500 ppm (parts per million) within the interior and/or within the disclosed system. In some embodiments, the generator can produce UV light to sanitize the contents of the interior of the enclosure and the associated CPAP equipment. To this end, the generator can include one or more ultraviolet lights that can be activated for a pre-set time period. UV light is highly effective at deactivating microorganisms, including bacteria, viruses, yeasts, and molds. In some embodiments, the UV light is in the range of about 100-280 nanometers which is known to damage the DNA molecules in bacteria, viruses, molds, yeasts, and other microorganisms, preventing them from replicating and causing harm.

The sanitizing enclosure can kill about 99% of mold, bacteria, and viruses in the CPAP user's sockets (or mask), tubing, humidifier, and CPAP chamber. In addition to being highly effective, the sanitizing enclosure is designed for ease of use. Users simply place their sockets or mask in the sanitizing enclosure, close the lid, and walk away. Importantly, no disassembly of the CPAP apparatus is required prior to start of the sanitizing process. Advantageously, the sanitizing enclosure can be used daily. In one embodiment, the sanitizing enclosure is configured to support several sanitization cycles to be carried out per day. The enclosure can be configured in any desired shape, such as circular, oval, square, triangular, oval, hexagonal, pentagonal, star, abstract, and the like. The enclosure can be configured in any desired size. In some embodiments, the enclosure can have a relatively small size, compared to the size of the CPAP assembly. For example, the enclosure can have a height, width, and depth of less than about 5 inches, such as no more than about 5.0, 4.75, 4.5, 4.25, 4.0, 3.75, 3.5, 3.25, 3.0, 2.75, 2.5, 2.25, 2.0, 1.75, 1.5, 1.25, or 1.0 inches. However, the enclosure can have any desired size to accommodate a particular CPAP element within its interior.

Figure 15A:
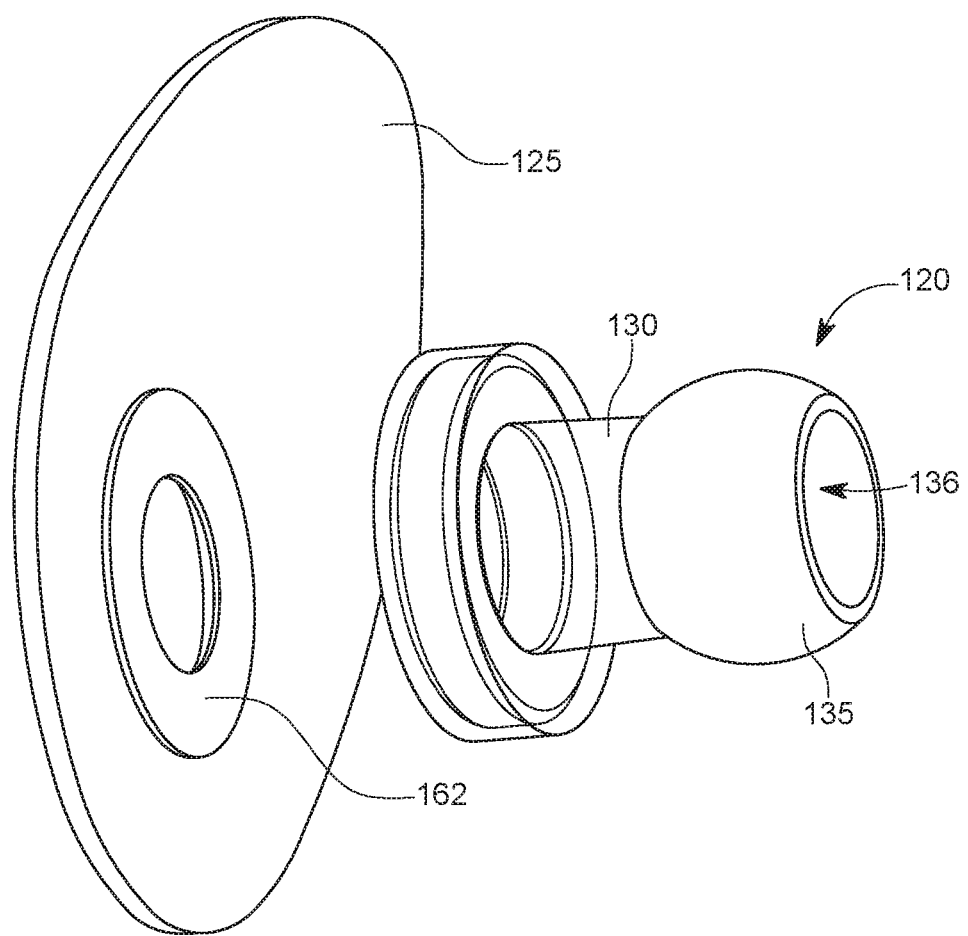
FIG. 15A is a side perspective view of a sheet and a port magnet post that can be used with the disclosed nasal respiratory assembly in some embodiments.
Figure 15B:
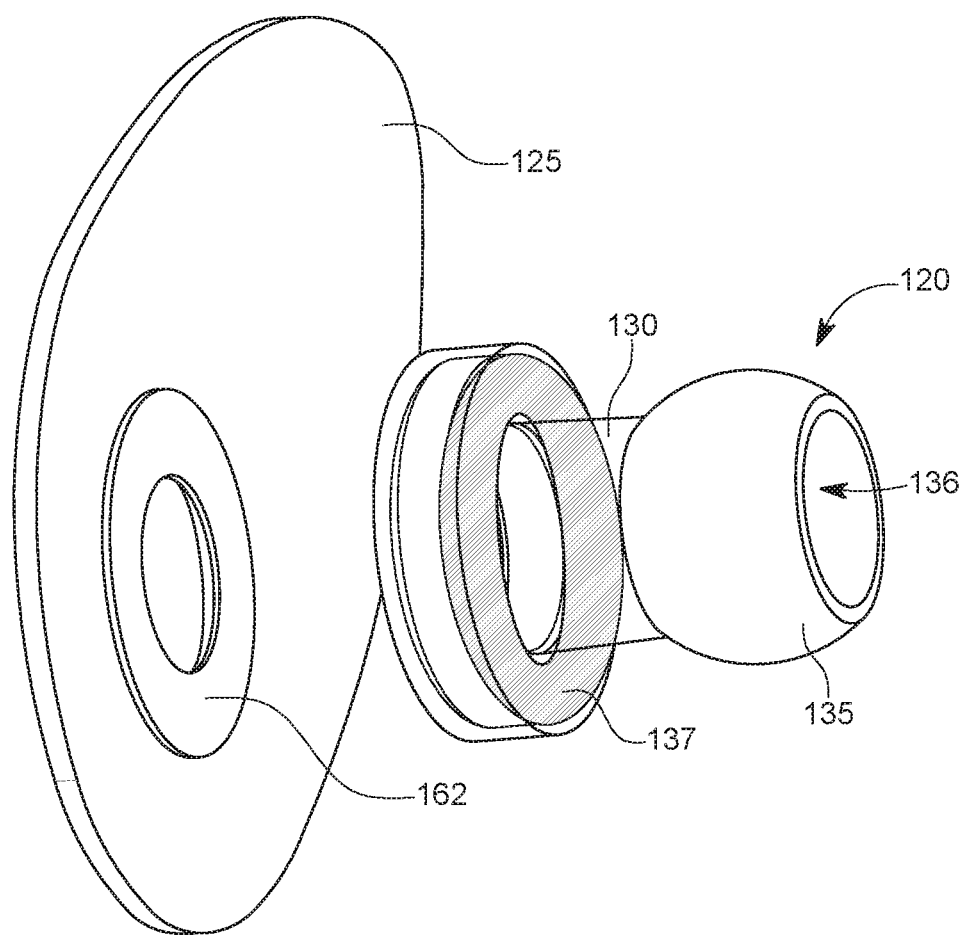
FIG. 15B is a side perspective view of a sheet and a port magnet post including an additional ball and socket arrangement that can be used with the disclosed nasal respiratory assembly in some embodiments.
Figure 16:
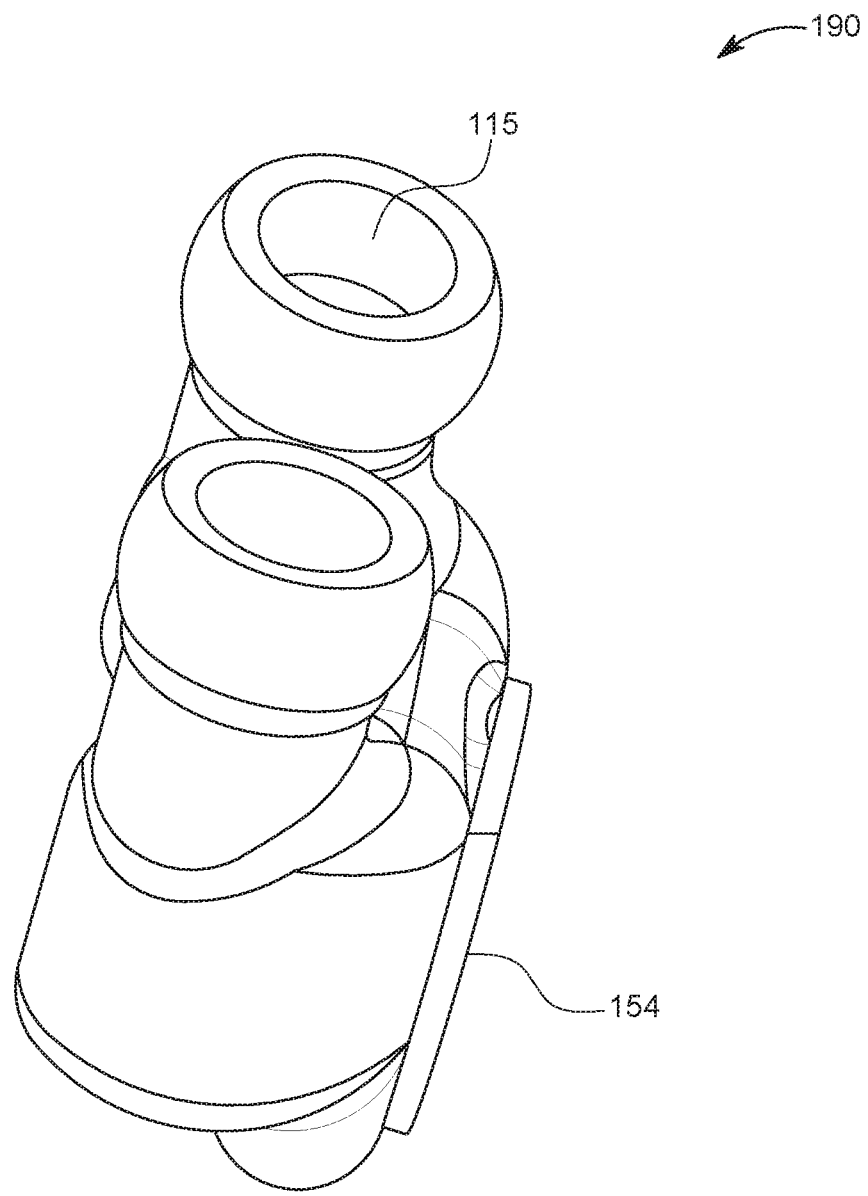
FIG. 16 is a top perspective view of a nasal connector that can be used with the disclosed nasal respiratory assembly in some embodiments.
Figure 17:
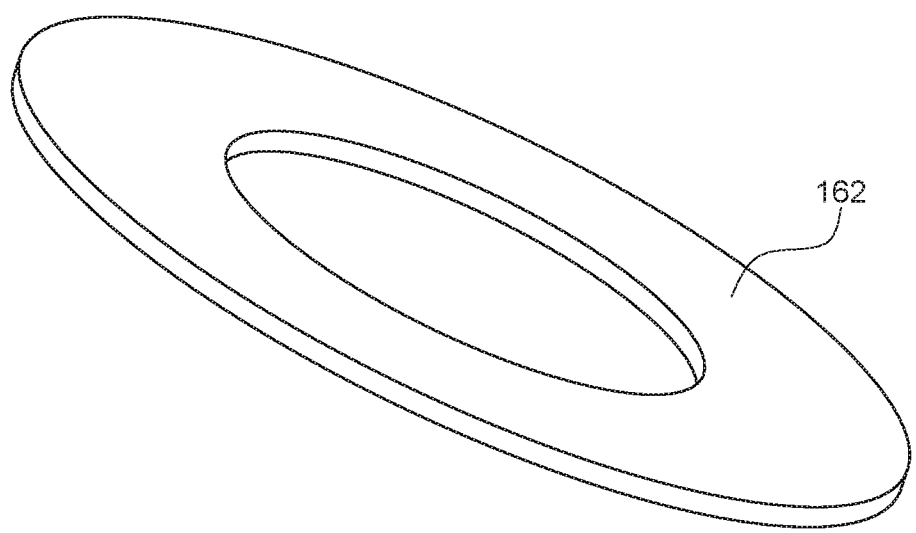
FIG. 17 is a side perspective view of a ferromagnetic ring that can be used with the disclosed ferromagnetic ring in some embodiments.
Figure 18:
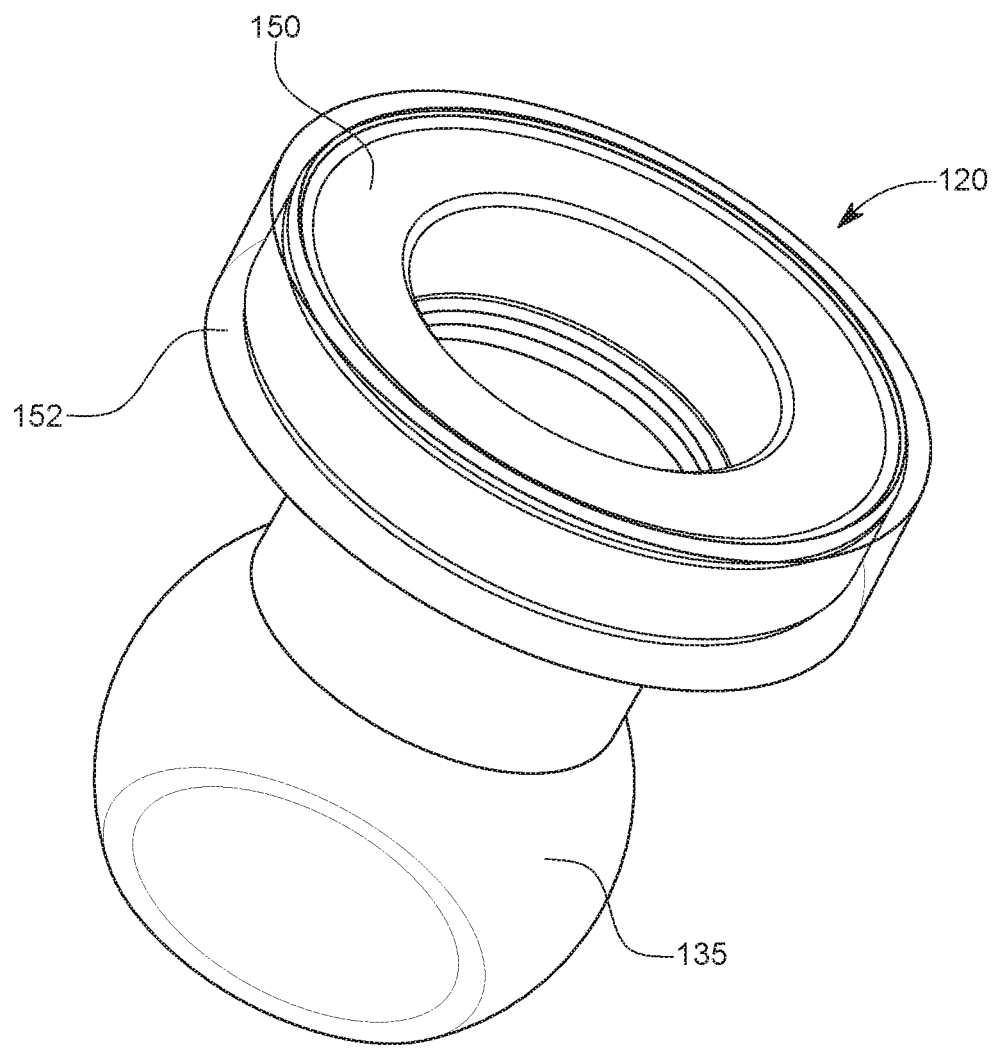
FIG. 18 is a side perspective view of a port magnet post that can be used with the disclosed ferromagnetic ring in some embodiments.
Figure 19:
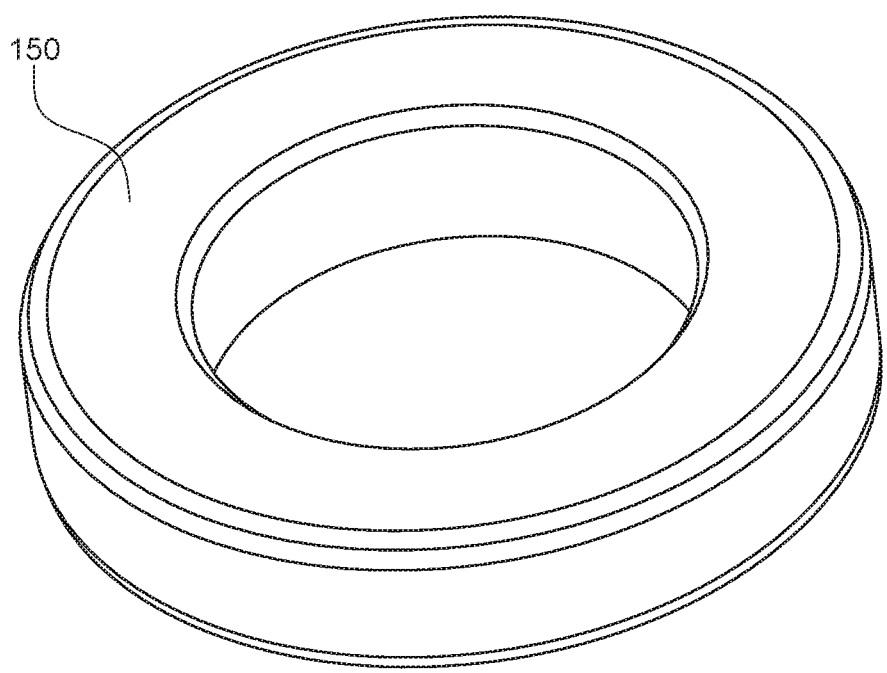
FIG. 19 is a side perspective view of a magnet that can be used with the disclosed assembly in some embodiments.

FIGS. 12 to 19 illustrate the components of nasal respiratory assembly 105 according to one or more embodiments of the presently disclosed subject matter. Nasal respiratory assembly 105 can have same or similar components as nasal respiratory assembly 5 except as explained herein. The primary differences of nasal respiratory assembly 105 over nasal respiratory assembly 5 illustrated in FIGS. 1 to 11 will now be explained. Instead of a ferromagnetic dome ring, nasal respiratory assembly 105 includes ferromagnetic ring 162 that has a substantially flat major surface facing post 120, as shown, for example, in FIG. 15A. Accordingly, a side of ferromagnetic ring 162 that faces magnet 150 (in the form of a magnetic ring) has a substantially flat surface. Further, post 120 of nasal respiratory assembly 105 includes a ball shaped receptacle 135 that cooperates with socket opening 115 of nasal connector 190 in a ball and socket arrangement, as shown, for example, in FIG. 15A. The ball shaped receptacle 135 is configured to pivotably move or rotate about an inner surface of socket opening 115 while still maintaining a substantially airtight connection therewith. In some embodiments, as illustrated in FIG. 16, for example, vent coupling 154 may be positioned on a side surface of the nasal connector 190 (as opposed to being provided on a bottom surface of the nasal connector). Ferromagnetic ring 162 that has a substantially flat major surface as illustrated, for example, in FIG. 15A, can allow for a sliding movement of magnet 150 across ferromagnetic ring 162 to enable a convenient disconnect mechanism. In one embodiment wherein ferromagnetic ring 162 is itself a permanent magnet (rather than ferromagnetic ring 162 being formed of a material that magnet 150 attracts), the polarity of magnet 150 exhibits a pull or push magnetic force against ferromagnetic ring 162 depending on the polarity of the corresponding ferromagnetic ring 162. This pull or push force can be advantageously designed for the convenient connecting or disconnecting of ferromagnetic ring 162 to/from magnet 150.

Magnet 150 removably attaches to the ferromagnetic ring 162 at an exit end of post 120. In one embodiment, magnet 150 is configured to move or rotate about the surface of ferromagnetic ring 162 while continuing to maintain a substantially airtight connection at the interface between magnetic 150 and ferromagnetic ring 162. The ferromagnetic ring 162 can thus advantageously prevent or reduce the possibility of the nasal connector 190 from inadvertently getting dislodged when the wearer of the nasal respiratory assembly 105 moves the head either when awake or sleeping to thereby allowing for the continued supply of treatment gases to a patient's (or wearer's) nare under ideal pressure. In at least one embodiment, the ferromagnetic ring 162 can permit magnet 150 to move or rotate about the surface of ferromagnetic ring 162 while continuing to maintain a substantially airtight connection therewith when the face of a patient wearing nasal respiratory assembly 105 is moved in a sudden jerky movement. In at least one embodiment, the ferromagnetic ring 162 can permit magnet 150 to move or rotate about the surface of ferromagnetic ring 162 while continuing to maintain a substantially airtight connection therewith when the wearer's pillow contacts or applies a shearing force against a portion of the nasal respiratory assembly 105 or against the tubing supplying fluid to the nasal respiratory assembly 105.

In an alternate embodiment, as shown, for example in FIG. 15B, post 120 includes an additional ball and socket arrangement 137 positioned directly below magnet 150, with ball and socket arrangement 137 being arranged between magnet 150 and an upper end of post body 130 (i.e., an end of post body 130 that faces sheet 125). The ball and socket arrangement 137 offers a pivoting head for magnet 150 to receive the ferromagnetic ring 162 (ferromagnetic ring 162 is separately illustrated in FIG. 17) at different pitches and angles for nares that flare on the outside of the nose, with each ball and socket arrangement 137 providing for the respective magnet 150 to pivot from angles 0-90 degrees relative to the upper end (i.e., at a sheet 125 facing end) of post body 130. Accordingly, as a person of skill in the art would understand, the ball shaped portion of ball shaped socket arrangement 137 is configured to pivotably move or rotate about an inner surface of a suitable cooperating socket arrangement provided at or near the upper end of post body 130 while still maintaining a substantially airtight connection therewith. In other words, the ball and socket arrangement 137 operates similar to how ball shaped receptacle 35 cooperates with channel opening 15 of nasal connector 90 in a ball and socket arrangement in nasal respiratory assembly 5. The ball and socket arrangement 137 can further operate similar to how ball shaped receptacle 135 cooperates with an inner surface of socket opening 115 in a ball and socket arrangement in nasal respiratory assembly 105.

The remaining components of nasal respiratory assembly 105 may be substantially similar to or identical to the respective components of nasal respiratory assembly 5, with the components of nasal respiratory assembly 105 labeled with numerals that include a 100th place prefix "1" added to the respective components of nasal respiratory assembly 5. For example, magnet 150 of nasal respiratory assembly 105 can be substantially similar or identical features as magnet 50 of nasal respiratory assembly 5. As another example, vent coupling 154 of nasal respiratory assembly 105 can be substantially similar or identical features as vent coupling 54 of nasal respiratory assembly 5, and so on. Accordingly, nasal respiratory assembly 105 and its various components including opening 117, magnet socket 152, sheet 125, channel 136, nasal connector 190, vent 170, post 120 can have similar or identical features as the respective components of nasal respiratory assembly 5 arrived by excluding the 100th place prefix "1" from the corresponding components of nasal respiratory assembly 105, except as otherwise explained herein.

Accordingly, nasal respiratory assembly 105 comprises a pair of sheets 125, each sheet defining an opening 117 sized and shaped to fit over the nostril of a patient, with a ferromagnetic ring 162 positioned at an underside of the sheet and circumferentially aligned with the opening, with an upper side of the sheet configured for sealable engagement with the nostril. A pair of posts such as posts 120, each post including a magnet 150 (e.g. in the form of a magnetic ring) positioned at a first end and a ball shaped receptacle 135 positioned at a second end with a passageway extending from the first to the second ends, the magnet 150 removably attachable to the ferromagnetic ring 162. A nasal connector 190 with a pair of socket openings 115 at a post end, each socket opening 115 sized and shaped to receive the ball shaped receptacle 135 in a ball and socket arrangement to form a substantially airtight connection therewith, and an inlet such as vent coupling 154 at a vent end that is fluid communication with a flexible tubing connected to a fluid source.

Figure 20:
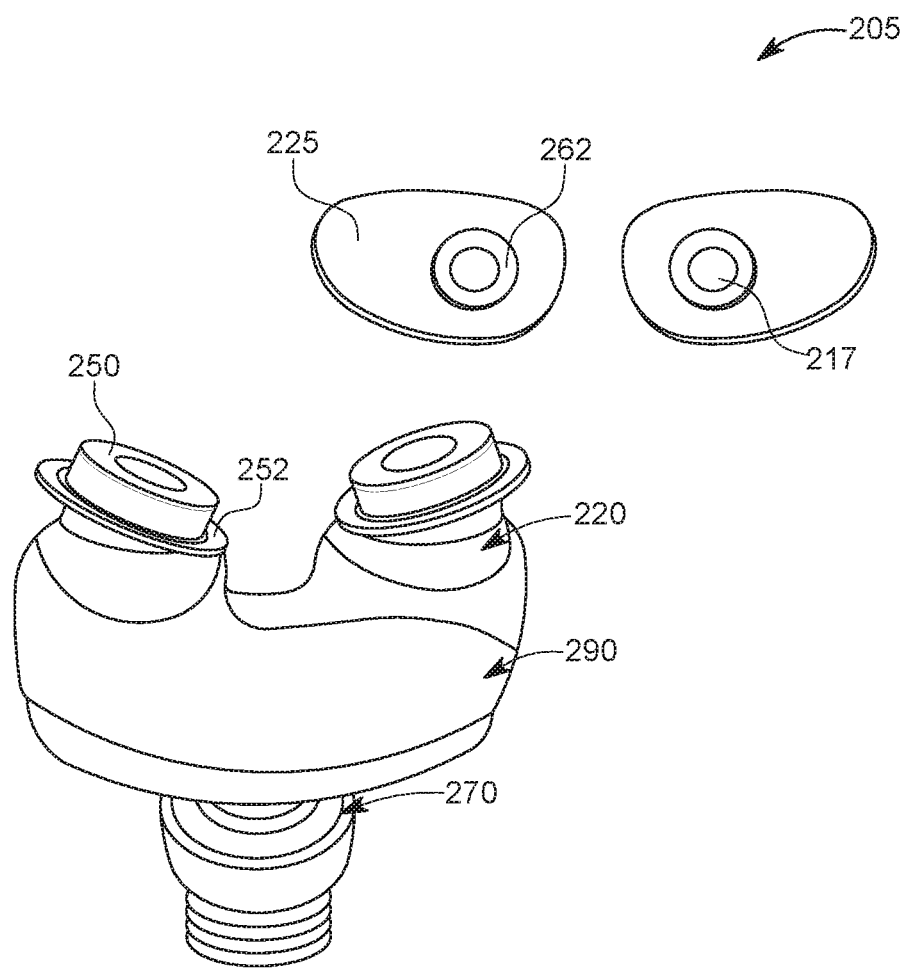
FIGS. 20 and 21 are perspective views of a nasal respiratory assembly in accordance with some embodiments.

FIGS. 20 and 21 illustrate the components of a nasal respiratory assembly such as nasal respiratory assembly 205 according to one or more embodiments of the presently disclosed subject matter. Nasal respiratory assembly 205 can have same or similar components as nasal respiratory assembly 105 except as explained herein. The primary differences of nasal respiratory assembly 205 over nasal respiratory assembly 105 illustrated in FIGS. 12 to 19 will now be explained. Post 220 of nasal respiratory assembly 205 includes a receptacle that cooperates with an opening of nasal connector 290 in a substantially airtight arrangement. In one embodiment, the vent 270 of nasal respiratory assembly 205 may not include an L-bend unlike vent 170 of nasal respiratory assembly 105. Further, ferromagnetic ring 262 may or may not have a dome shape. The upper surface of post 220 is angled as illustrated, for example, in FIG. 20. Magnet socket 252 is positioned about a first end of the post 220. In some embodiments, magnet socket 252 (e.g., an upper surface the post 220) can be angled in relation to the body of post 220 to allow for enhanced attachment to ferromagnetic ring 262 of sheet 225 for better positioning on a patient's nostrils (see FIG. 20, for example). In some embodiments, the angle can be between about 0-45 degrees, such as about 5, 10, 15, 20, 25, 30, 35, 40, or 45 degrees. For example, in some embodiments, a plane parallel to a circumference, a perimeter, or a largest dimension of the magnet socket 252 can be configured to make an angle of about 0-45 degrees with a plane that is perpendicular to a vertical axis passing through the center of a bottom portion of the channel provided by port magnet post 200 that is closest to the channel openings of the nasal connector 290. As another example, in some embodiments, a plane parallel to a circumference, a perimeter, or a largest dimension of the magnet socket 252 can be configured to make an angle of about 0-45 degrees with a major lateral plane that is perpendicular to a vertical axis passing through the center of the opening provided on vent 270. In some embodiments, the angle can be created by having a portion of the post body bulge outwards at an angle. In some embodiments, the angle can be created by modifying one or more components of nasal connector 290, including the area directly beneath the channel opening of post 220. Alternatively, in some embodiments, the body of post 220 can remain substantially cylindrical, having a top portion cut at an angle. The body of post 220 (that shares features of post body 30 of post 20) houses a channel within its interior to allow the flow of fluid to the nasal cavity of the patient. In some embodiments, the body can have a circular, oval, or square cross-sectional shape. However, the shape of the body is not limited and can be configured in any desired shape. Further, the channel of post 220 (that shares features with channel 36 of post 20) can have any desired cross-sectional shape, such as square, triangular, circular, oval, and the like. Magnet socket 252, magnet 250 and opening 217 too can take various cross-sectional shapes. According to one or more embodiments, an upper surface of the magnetic ring is angled. In such embodiments, the magnetic ring can have different thicknesses in different regions of the magnetic ring. The remaining components of nasal respiratory assembly 205 may have substantially similar or identical features as the respective components of nasal respiratory assembly 105, with the components of nasal respiratory assembly 205 labelled with numerals that include a 100th place prefix of "2" instead of "1" used to label respective parallel components of nasal respiratory assembly 105. For example, magnet 250 of nasal respiratory assembly 205 can be substantially similar to or identical to magnet 150 of nasal respiratory assembly 105, As a further example, vent 270 of nasal respiratory assembly 205 can be substantially similar to or identical to vent 170 of nasal respiratory assembly 105, and so on. Accordingly, nasal respiratory assembly 205 and its various components including sheet 225, nasal connector 290, post 220 can have similar or identical features as the respective parallel components of nasal respiratory assembly 105 except as otherwise provided herein.

Accordingly, nasal respiratory assembly 205 comprises a pair of sheets 225, each sheet 225 defining an opening sized and shaped to fit over the nostril of a patient, with a ferromagnetic ring 262 positioned at an underside of the sheet 225 and circumferentially aligned with the opening, with an upper side of the sheet configured for sealable engagement with the nostril. A pair of posts such as post 220 are provided, each post including a magnet 250 (for example, in the form of a magnetic ring) positioned at a first end and a receptacle positioned at a second end with a passageway extending from the first to the second ends, the magnet 250 removably attachable to the ferromagnetic ring. A connector such as nasal connector 290 with a pair of channel openings at a post end, each channel opening sized and shaped to cooperate with one of the post receptacles to form a substantially airtight connection therewith, and an inlet at a vent end that is fluid communication with a flexible tubing such as tubing 10 connected to a fluid source.

Figure 22:
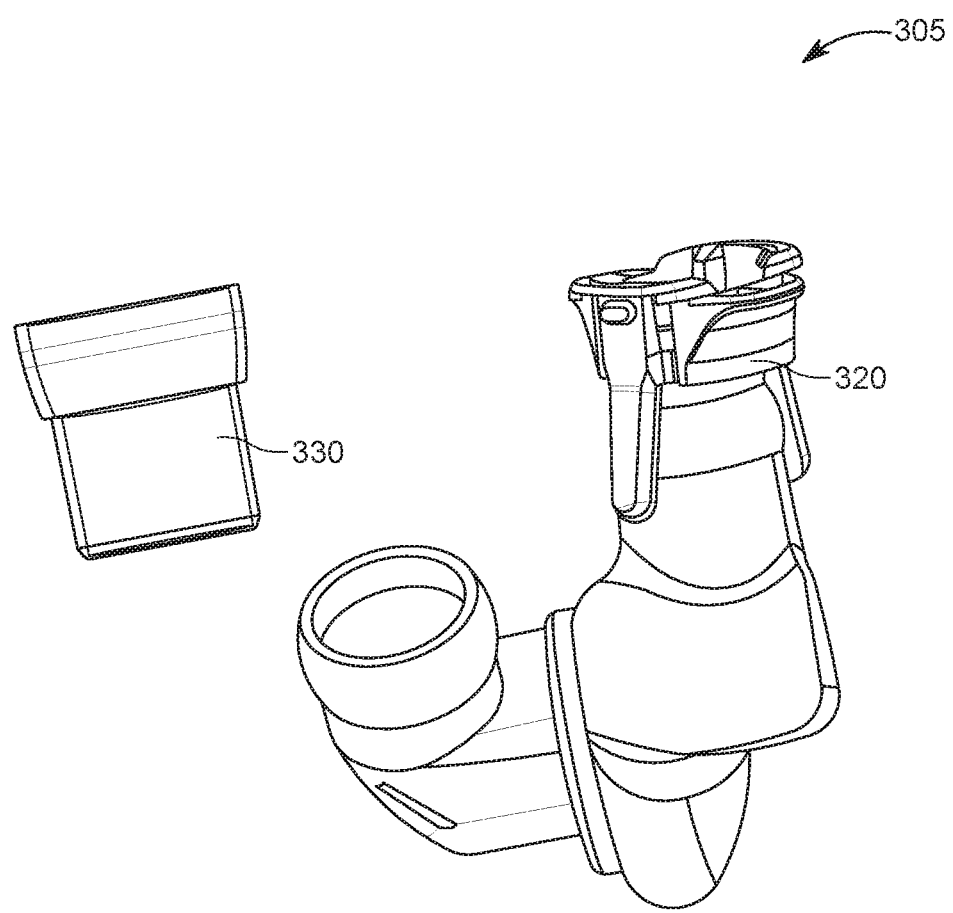
FIGS. 22 to 24 are perspective views of a nasal respiratory assembly in accordance with some embodiments.
Figure 23:
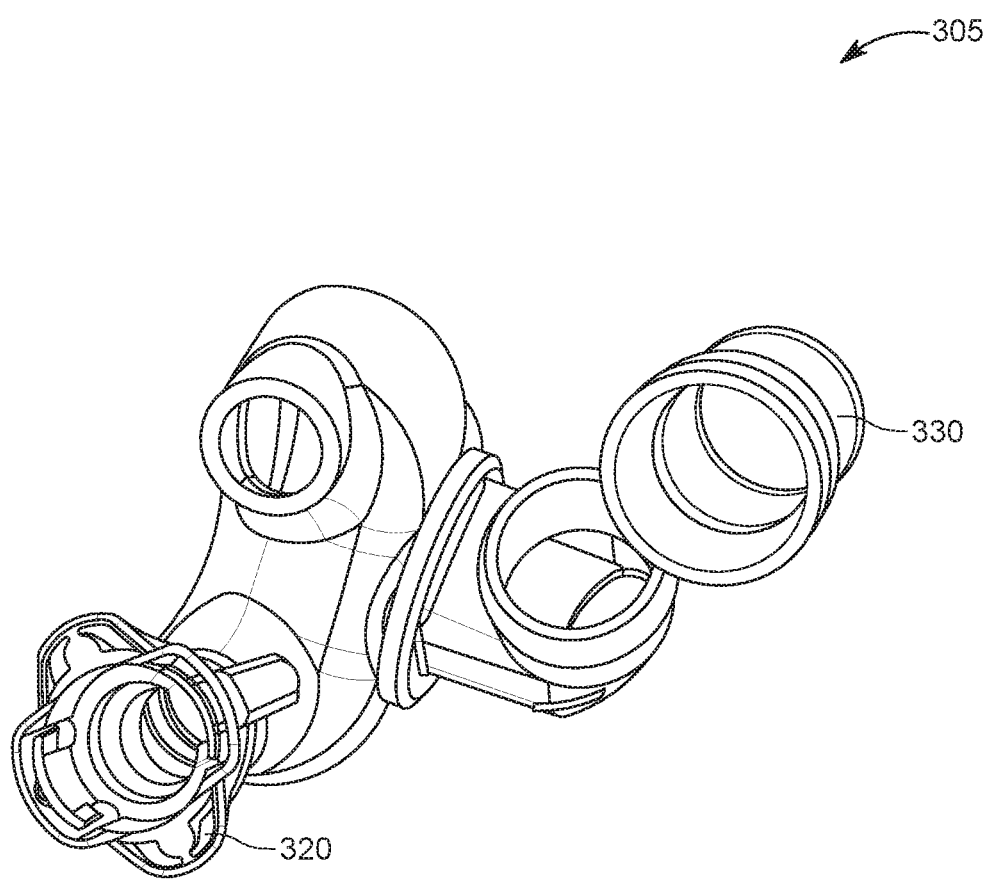
Figure 24:
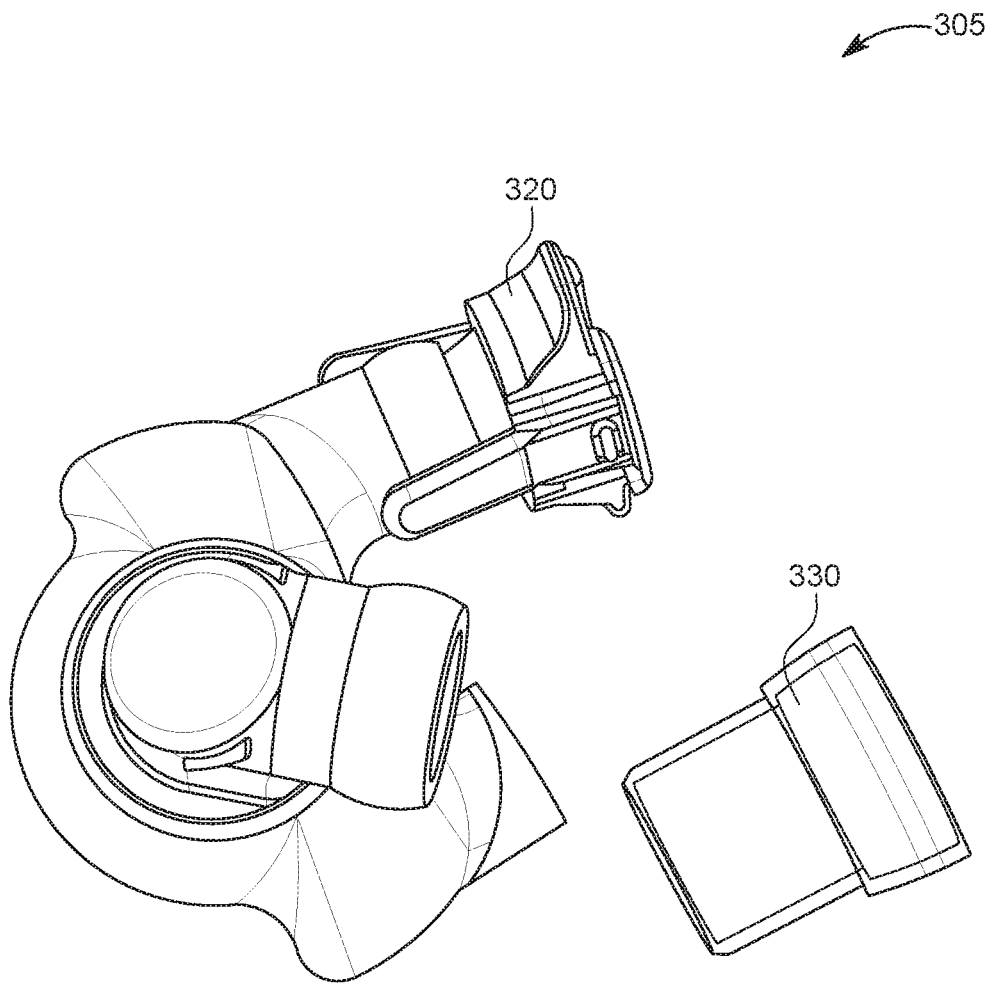

FIGS. 22 to 24 illustrate the components of nasal respiratory assembly 305 according to one or more embodiments of the currently disclosed subject matter. In some embodiments, as illustrated in FIGS. 22 to 24, for example, the channel openings of nasal respiratory assembly 305 can be configured as sockets that releasably connect with the posts of nasal respiratory assembly 305. Each socket can include one or more releases for engaging and disengaging the post from the socket such as snap-on connector 320 labeled in FIGS. 22 to 24. The releases can be in the form of any of the wide variety of connection mechanisms known or used in the art, including (but not limited to) snap fit, screw fit, friction fit, magnetic attraction, and the like. For example, in some embodiments, the release can be configured as one or more arms that extend from a collar end of the socket. The arms can be constructed at an angle to provide leverage when pivoting the arm, thereby enabling socket collar to be deformed away from the post positioned in a recess for easy release. Additionally, a conduit such as conduit 330 can be provided between vent 70 and tubing 10.

Figure 25:
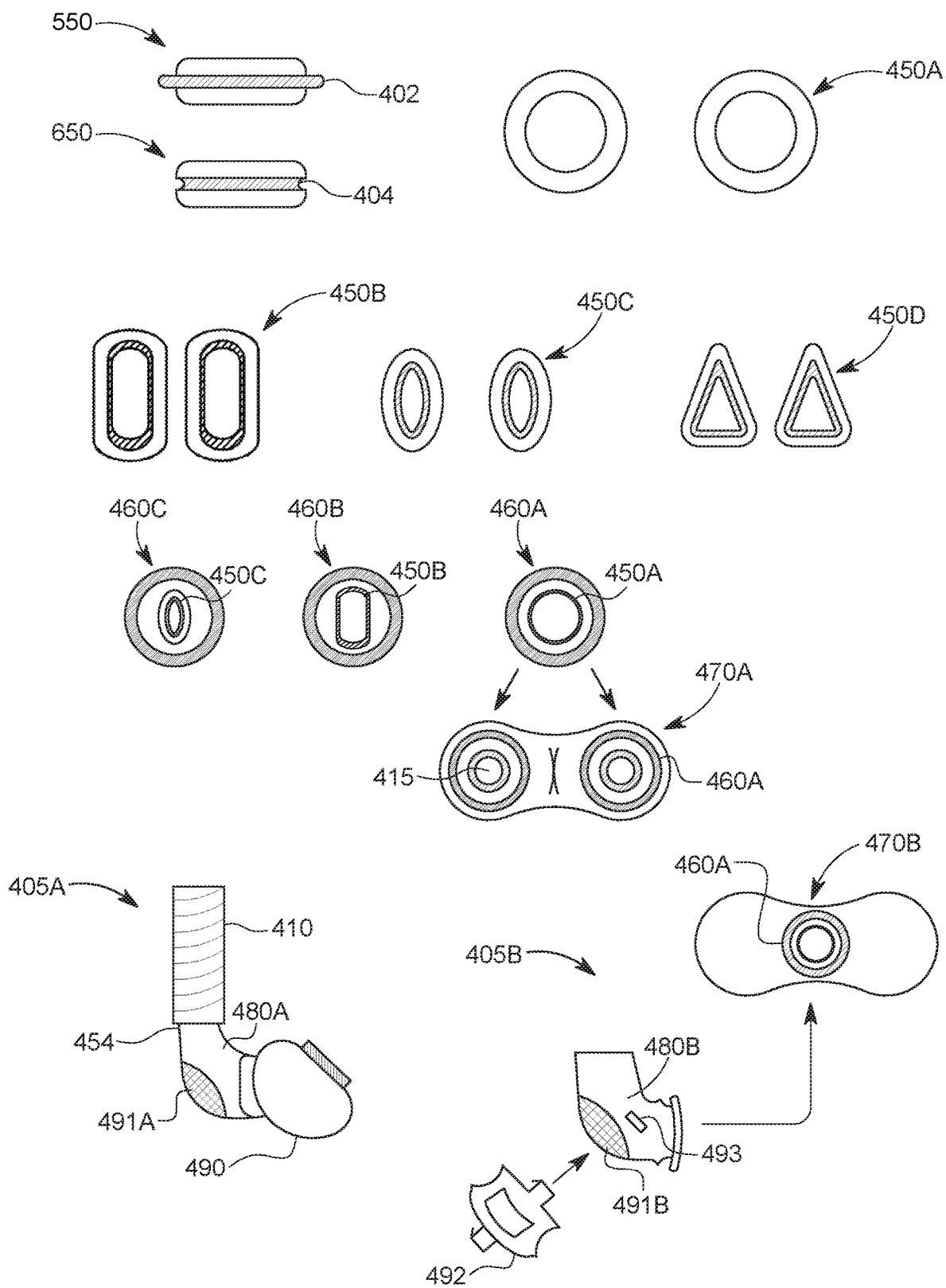
FIG. 25 includes schematic views of various components of a nasal respiratory assembly in accordance with some embodiments.
Figure 26:
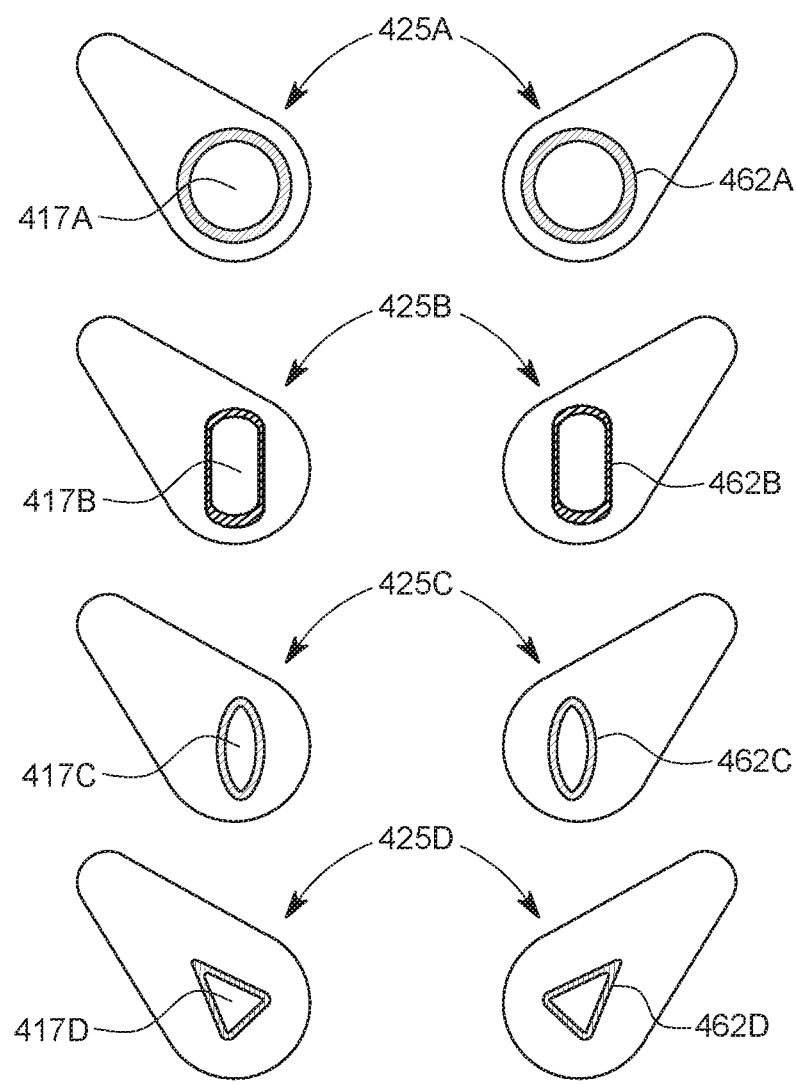
FIG. 26 includes schematic views of variable embodiments of a sheet including a ferromagnetic ring that can form part of a nasal respiratory assembly in accordance with some embodiments.

FIGS. 25 and 26 illustrate the components of nasal respiratory assembly 405A and nasal respiratory assembly 405B according to one or more embodiments of the presently disclosed subject matter. As illustrated in FIG. 25, nasal respiratory assembly 405A includes tubing 410 in fluid connection with hollow elbow 480A, with swivel coupling 454 operating to provide a substantially airtight connection between tubing 410 and elbow 480A. Swivel coupling 454 can conveniently allow one of elbow 480A and tubing 410 to pivotally move relative to the other.

The end of elbow 480A facing nasal connector 490 is sized and shaped to cooperate with a vent end of nasal connector 490 to form a substantially airtight connection therewith. Accordingly, through a hollow opening running through elbow 480A, the vent end of nasal connector 490 that faces elbow 480A is configured for fluid communication with flexible tubing 410 connected to a fluid source. Thus, in one embodiment, a hollow elbow such as elbow 480A is located between nasal connector 490 and flexible tubing 410.

Elbow 480A includes a $CO_2$ exhaust 491A sized and shaped to facilitate venting of CO2 exhaled by a patient wearing nasal respiratory assembly 405A. Similarly, elbow 480B includes a $CO_2$ exhaust 491B sized and shaped to facilitate venting of $CO_2$ exhaled by a patient wearing nasal respiratory assembly 405B. Each of nasal respiratory assembly 405A and nasal respiratory assembly 405B can further include a diffuser cap 492 that removably attaches to elbow 480A via protrusions provided on the diffuser cap that engage corresponding recessed notches 493 (see FIG. 25) provided on either sides of elbow 480A and elbow 480B, the recessed notches positioned diagonally across from each other. $CO_2$ exhaust 491A operates to ensure that the patient's ability to breathe is not hampered, and to ensure excess fluid has an outlet. $CO_2$ exhaust 491A can be sized and shaped in any desired configuration and can be positioned proximal to any of the regions where fluid flow occurs. $CO_2$ exhaust 491A can vary in size and location such that manipulation of all exhaled fluids (e.g., carbon dioxide) is controlled and titratable to alter the flow rate to a desired setting. In some embodiments, $CO_2$ exhaust 491A can include polymeric fibers, membranes, and/or webs with an extremely small thickness (e.g., from nanoscale to microscale).

Nasal connector 490 can be constructed of silicone or similar other flexible material according to one or more embodiments of the presently disclosed subject matter. A sheet of nasal connector 490 located on the side of nasal connector 490 opposite to the vent end (i.e., the end opposite to the end facing elbow 480A) includes a flange such as flange 470A, as shown in FIG. 25. Flange 470A present on the sheet end of nasal connector 490 can include silicone or a similar other flexible material according to one or more embodiments of the presently disclosed subject matter. As shown in FIG. 25, flange 470A accommodates two slip rings such as slip rings 460A, 460B, 460C or 460D securely held therein, with flange 470A comprising a silicone sheet or a similar other material. Each slip ring 460A, 460B, 460C or 460D securely holds therein a respective magnet 450A, 450B, 450C or 450D. As shown in FIG. 25, magnet 550 includes a ridge 402 that circumferentially surrounds magnet 550, and magnet 650 includes a groove 404 that circumferentially surrounds magnet 650, In various embodiments, each magnet 450A, 450B, 450C or 450D may be provided with either a groove 404 or a ridge 402 that circumferentially surrounds the magnet. Groove 404 or ridge 402 of magnet 450A, 450B, 450C or 450D operates to provide an increased secure coupling between magnet 450A, 450B, 450C or 450D and a respective slip ring 460A, 460B, 460C or 460D. Each slip ring is made of a flexible material. In some embodiments, each slip ring can include a material such as LDPE (low density polyethylene) at or near its inner edge that holds magnet 450A, and a material such as styrene butadiene copolymer (SBC) sold under the trade name K-Resin® at or near it outer edge. This combination of materials forming part of the slip ring can advantageously permit round magnet 450A, for example, to swivel within and about a respective slip ring 460A while fixed attached thereto. In other words, the materials used in the construction of slip ring 460A, 460B, 460C or 460D can conveniently provide for magnet 450A, 450B, 450C or 450D to pivotally move relative to the respective slip ring 460A, 460B, 460C or 460D that holds the magnet 450A, 450B, 450C or 450D. In some embodiments, the slip ring can further include a soft playable membrane that surrounds the magnet and fills the remaining void inside each slip ring between its outer and inner edges to help increase the comfort for the patient wearing nasal respiratory assembly by reducing or eliminating the torque that may otherwise be felt at the nose of the patient of the assembly during use of the assembly by the patient. In some embodiments, the soft playable membrane may include silicone or as similar other material that can conveniently reduce or eliminate the torque that may otherwise be felt at the nose of the patient of the assembly during use of the assembly by the patient. In some embodiments, the whole of the slip ring may consist of only the magnet 450A, 450B, 450C or 450D and the soft playable membrane that surrounds the magnet and fills the whole void inside the slip ring.

In some further embodiments, an inner portion of the space between an outer perimeter of the magnet and the outer contour of the slip ring (i.e., the portion contiguous to the outer perimeter of the magnet) includes a slender, loose, extremely flexible, and forgiving thin-layer of silicone that is configured to bounce in an out relative to the slip ring or relative to the magnet to help accommodate movements initiated by the patient during use of the nasal respiratory assembly to reduce torque. In the same embodiments, an outer portion of the space between an outer perimeter of the magnet and the outer contour of the slip ring (i.e., the portion contiguous to the outer perimeter of the slip ring) can include a silicon layer that is less slender, less flexible and thicker relative to the portion that is contiguous to the outer perimeter of the magnet. Further, the material of the flange 470A directly adjoining and encircling the slip ring too can include a silicon layer that is less slender, less flexible and thicker relative to the portion that is contiguous to the outer perimeter of the magnet. Such an arrangement can help further increase the comfort level for the patient wearing nasal respiratory assembly by reducing or eliminating the torque that may otherwise be felt at the nose of the patient of the assembly during use of the assembly by the patient.

In various embodiments, the outer perimeter of slip rings 460A, 460B, and 460C may be of a standard dimension, whereas the dimensions of the perimeter of the inner opening of the slip rings can vary, with the size and shape of the inner opening configured and adapted for the respective magnet to be received therein; in other words, the inner opening of the slip ring is sized and shaped for securely holding the magnet to be received therein. Thus, the dimensions of the inner opening cane be different for each of round magnet 450A, oblong magnet 450B, oval magnet 450C and tear drop magnet 450D.

Each of magnets 450A, 450B, 450C or 450D can magnetically attach with a respective ferromagnetic ring 462A, 462B, 462C or 462D (see FIG. 26) of sheet 425A, 425B, 425C or 425D (see FIG. 26) through magnetic attraction forces to form a substantially airtight connection therewith. Provision of ferromagnetic rings 462A-462D of various circumferential shapes laid onto sheets 425A-425D can allow for an improved patient experience when integrated into a nasal respiratory assembly 405A or nasal respiratory assembly 405B capable of being installed upon a patient.

For example, round magnet 450A held in place by slip ring 460A magnetically attaches to ferromagnetic ring 462A (see FIG. 26) of sheet 425A (see FIG. 26) to form a substantially airtight connection therewith. During use of the nasal respiratory assembly 405A by a patient, when round magnet 450A is detachably attached to ferromagnetic ring 462A of sheet 425A (see FIG. 26), upper ends of channel openings 415 on round magnets 450A of nasal connector 490 are in fluid communication with the interior of the nostrils of the wearer, whereas the lower ends of channel openings 415 are in fluid communication with the interior of nasal connector 90 such that respiratory fluid flows from tubing 410, through elbow 480A, through each channel opening 415 of flange 470A, and through opening 417A of each sheet 425A and into the interior of the nostrils of the wearer. Thus, each channel opening 415 comprises a unique pathway for conveying fluid from a fluid source to the nasal passage of the patient.

Nasal respiratory assembly 405A can further include a pair of sheets such as sheet 425A, 425B, 425C or 425D, each sheet defining an opening sized and shaped to fit over the nostril of a patient, with a respective ferromagnetic ring 462A, 462B, 462C or 462D positioned at an underside of the sheet and circumferentially aligned with the opening, with an upper side of the sheet configured for sealable engagement with the nostril. Channel opening 415 of round magnet 450A has a circular cross-section, which compliments/matches the circular cross-section of opening 417A of sheet 425A. Channel opening 415 of round magnet 450B has an oblong cross-section, which compliments/matches the oblong cross-section of opening 417B of sheet 425B. Channel opening 415 of round magnet 450C has an oval cross-section, which compliments/matches the oval cross-section of opening 417C of sheet 425C. Channel opening 415 of round magnet 450D has a tear drop cross-section, which compliments/matches the tear drop cross-section of opening 417D of sheet 425D. Accordingly, each of magnets 450A, 450B, 450C or 450D is configured to engage with a respective ferromagnetic ring 462A, 462B, 462C or 462D (see FIG. 26) of sheet 425A, 425B, 425C or 425D (see FIG. 26). Each sheet 425A, 425B, 425C or 425D is configured to engage a nostril of the patient. Each sheet 425A, 425B, 425C or 425D directly contacts the exterior of a patient's nostril or the skin surrounding the patient's nostril. The sheets can be configured for providing a flush, sealable engagement with the patient's nares.

In various embodiments, each sheet 425A, 425B, 425C or 425D engages with or includes one or more flexible adhesive sheets (not shown) to provide sealable engagement with the patient's nostrils. Sheet 425A, 425B, 425C or 425D can be constructed from any known material, including (but not limited to) woven fabric, plastic, and/or latex. For example, in some embodiments, sheet can be constructed from PVC, polyethylene, polyurethane, latex, or combinations thereof. In some embodiments, sheet 425A, 425B, 425C or 425D can be a foam medical tape, a surgical tape, and/or a hypoallergenic tape. The patient contacting surface of sheet 425A, 425B, 425C or 425D can include an adhesive. The adhesive can be any medically safe adhesive known or used in the art. For example, the adhesive can be selected from one or more acrylates (such as methacrylate, alkyl acrylate, or epoxy diacrylate), acrylic acids, polyvinyl chloride, alkyl esters, or combinations thereof. In some embodiments, the adhesive is a pressure-sensitive adhesive such that the sheet can be adhered and removed from the patient's skin as desired. The adhesive can be selected to show mild or no irritation to the skin when used daily. In some embodiments, the adhesive tape can be configured as a hydrocolloid tape and/or can include a polyurethane reactive layer that adheres more to the nostril as the patient's body temperature warms up the adhesive. Alternatively, in some embodiments, the adhesive can be directly applied to the patient's nostril or the nasal engaging portion to provide a removeable connection (e.g., no sheet is used). In various embodiments, each sheet 425A, 425B, 425C or 425D or the adhesive present therein is configured to match the shape of each respective magnet 450A, 450B, 450C or 450D (shown in FIG. 25).

In various embodiments, providing for the magnets 450A, 450B, 450C or 450D to rest directly or indirectly against or near a surface of the nose can significantly reduce torque. Additionally, the ability of magnets 450A, 450B, 450C or 450D to shift and spin will help in significantly reducing torque. In other words, the ability of magnets 450A, 450B, 450C or 450D to pivotally move relative to a spin ring 460A, 460B, 460C or 460D that securely holds the magnet 450A, 450B, 450C or 450D while the respective magnet 450A, 450B, 450C or 450D maintains an airtight connection with a respective ferromagnetic ring 462A, 462B, 462C or 462D can help increase the comfort for the patient wearing nasal respiratory assembly by reducing or eliminating the torque that may otherwise be felt at the nose of the patient of the assembly during use of the assembly by the patient.

Accordingly, in various embodiments, nasal respiratory assembly 405A comprises a pair of sheets 425C, each sheet 425C defining an opening sized and shaped to fit over the nostril of a patient, with a ferromagnetic ring 462C positioned at an underside of the sheet and circumferentially aligned with the opening, with an upper side of the sheet 425C configured for sealable engagement with the nostril. Nasal respiratory assembly 405A further comprises a nasal connector 490 including a pair of slip rings 460C at a sheet end, each slip ring 460C including a magnets 450C defining a channel opening 415, the magnets 450C configured to pivotably tilt about the slip ring 460C, each magnet 450C sized and shaped to removably attachable to one of the ferromagnetic rings 462C to form a substantially airtight connection therewith, and an inlet at a vent end that is fluid communication with a flexible tubing 410 connected to a fluid source, wherein the channel opening has an oval shape. In various embodiments, the channel openings can also have a round, oblong, oval or tear drop or a similar other shape. The opening of the ferromagnetic ring can have a shape that compliments/matches the shape of the channel opening of the magnetic ring. For example, the opening 417C of the ferromagnetic ring 462C can have an oval shape that compliments/matches the oval shape of the channel opening of the magnetic ring.

Nasal respiratory assembly 405A can further comprise hollow elbow 480A connecting the inlet at the vent end of the connector to flexible tubing 410 connected to the fluid source. In some embodiments, swivel coupling 454 can connect hollow elbow 480A to flexible tubing 410.

The bottom right side of FIG. 25 further illustrates a nasal respiratory assembly 405B according to one or more embodiments of the presently disclosed subject matter. Nasal respiratory assembly 405B can have same or similar components as nasal respiratory assembly 405A except as explained herein. Nasal respiratory assembly 405B may omit a nasal connector such as nasal connector 490; in other words, in nasal respiratory assembly 405B, flange 470B may attach directly to a sheet end of elbow 480B, the sheet end being positioned opposite to the side of elbow 480B that includes swivel coupling 454. Swivel coupling 454 connects to tubing 410 such that swivel coupling 454 can allow for tubing 410 to swivel relative to elbow 480B. $CO_2$ exhaust 491B can be configured similar to, or identical to $CO_2$ exhaust 491A. In some embodiments, nasal respiratory assembly 405B can include pairs of tubing 410, elbow 480B, and flange 470B—one for each nostril. In some embodiments, flange 470B can include two slip rings on a same single flange, as shown, for example, with regard to flange 470A of FIG. 25. Nasal respiratory assembly 405B can be otherwise be similar or identical to, and operate similar as, nasal respiratory assembly 405A in all other respects.

The remaining components of nasal respiratory assembly 405A and nasal respiratory assembly 405B can have substantially similar or identical features as the respective components of nasal respiratory assembly 105, with the components of nasal respiratory assembly 405A/405B labelled with numerals that include a 100th place prefix of "4" instead of "1" used to label respective parallel components of nasal respiratory assembly 105. For example, magnet 450 of nasal respiratory assembly 405A/405B can be substantially similar to or identical to magnet 150 of nasal respiratory assembly 105. As a further example, sheet 425 of nasal respiratory assembly 405A/405B can be substantially similar to or identical to sheet 125 of nasal respiratory assembly 105, and so on.

In various embodiments, the fluid source connected to tubing 10 can comprise a high flow oxygen (HFO) source, and the nasal respiratory assembly 5/105/205/305 and other components of the assembly as described herein can be used in combination with, or comprise one or more attributes of, a high-flow nasal cannula (HFNC). Accordingly, in various embodiments, the various nasal respiratory assemblies as described herein are configured to operate in conjunction with a HFNC system designed to deliver air flow that has been humidified such as, for example, the equipment manufactured by Salter Labs (Adult High Flow Cannula 1600HF with an effective delivery of oxygen flows up to 15 LPM), Vapotherm (2000i High Flow Therapy system with a flow range up to 40 LPM with 95% to 100% relative humidity and a temperature range of 33° to 43° C.), Teleflex (Comfort Flo Humidification System with flow rates up to 40 LPM), and Fisher & Paykel Healthcare (Optiflow™ and AIRVO™ 2 devices, both of which can deliver flow rates of up to 60 L/min).

As is well-known in the relevant art, an HFO system can deliver a high-flow air/oxygen blend through a nasal respiratory assembly such as nasal respiratory assembly 5, for example, thereby providing an alternative to other forms of ventilation. By providing flow rates of up to 60 LPM, high molecular humidity, and precise oxygen delivery, an HFO system can reduce the need for noninvasive ventilation and intubation in selected patient populations. The utilization of HFO therapy via a HFNC in appropriate patients can improve oxygenation, decrease the patient's work of breathing, and serve as an alternative to more invasive forms of treatment, such as mechanical ventilation. Most of the benefits from the HFNC, besides heating and humidification come from the optimal flow. HFNC provides for a continuous flow of fresh gas at high flow rates replacing or washing out the patient's pharyngeal dead-space (the old gas low in oxygen and high in CO2) whereby each breath that the patient now re-breathes will be washed out of carbon dioxide and replaced with oxygen rich gas improving breathing efficiency.

An HFO system can consist of a heated, humidified high-flow nasal cannula (HFNC) that can deliver up to 100% heated and humidified oxygen at a maximum flow of 60 LPM via nasal prongs or cannula. An air/oxygen blender can provide precise oxygen delivery independent of the patient's inspiratory flow demands. An HFO system can be utilized in a wide spectrum of patient care arenas; it can be administered to patient populations in critical care units, emergency departments, end-of-life scenarios, and in-home care environments. Improving gas exchange and decreasing work of breathing are clinical endpoints when managing patients with respiratory compromise. An HFO system can provide accurate oxygen delivery in a wide array of patient populations and treatment arenas, including when treating patients with mild to moderate hypoxemia. HFO therapy in appropriate patients can improve oxygenation and can decrease the patient's work of breathing without the need for noninvasive or invasive ventilation. In addition, it may reduce the duration of ICU stay in some patients. Humidified HFNC oxygen therapy can provide adequate oxygenation for many patients with hypoxemic respiratory failure and may be an alternative to NIV for patients who decline intubation. High-flow oxygen administration can also be utilized in the end-of-life clinical arena.

Heated and humidified oxygen has several benefits compared to standard oxygen therapy. Standard oxygen therapy delivered through a nasal cannula or another device, such as a non-rebreather mask (NRBM), delivers cold (not warmed) and dry (not humidified) gas. This cold, dry gas can lead to airway inflammation, increase airway resistance, and impair mucociliary function, possibly impairing secretion clearance. Also, a significant amount of energy is expended by individuals to both warm and humidify gas during normal breathing. Thus, heated, and humidified oxygen may improve secretion clearance, decrease airway inflammation, and decrease energy expenditure, particularly in the setting of acute respiratory failure. The use of the heated and humidified high-flow nasal cannula that is combined with an assembly as described herein can be advantageously used in the treatment of patients with respiratory failure through all age groups. In one example, the heat and humidified high-flow nasal cannula or high-flow nasal cannula (HFNC) can heat gas up to 37° C. with a 100% relative humidity, and can deliver 0.21-1.00% fraction of inspired oxygen (FiO2) at flow rates of up to 60 liters (L)/min. The flow rate and FiO2 can be independently titrated based on a patient's flow and FiO2 requirements. A key element for clinical use of nasal oxygen at s is accordingly its effective humidification.

Various embodiments of the presently disclosed subject matter can be used in conjunction with a high flow oxygen (HFO) source and/or a high-flow nasal cannula (HFNC). Embodiments that include a HFO source and/or a HFNC can advantageously include various aspects of the disclosed subject matter as described earlier including socket magnet posts such as posts 20 wherein one end of each post 20 is configured to removably attach to a ferromagnetic dome-shaped ring 62 on sheet 25 through the presence of a magnetic field. The other end of each post 20 can be configured to engage an opening of nasal connector 90. In various embodiments that include an HFO source and/or a HFNC, each post 20 can include a magnet 50 (e.g. in the form of a magnetic ring as shown in FIG. 1) positioned at a first end and a receptacle 35 positioned at a second end with a passageway extending from the first to the second ends. The magnet 50 can removably attach to the ferromagnetic dome-shaped ring 62 at exit end 16. In one embodiment that includes an HFO source and/or a HFNC, magnet 50 can be configured to pivotably move or rotate about the surface of ferromagnetic dome-shaped ring 62 in a ball and socket arrangement while continuing to maintain a substantially airtight connection at the interface between magnetic 50 and ferromagnetic dome-shaped ring 62.

In some embodiments that include an HFO source and/or a HFNC, the upper end of each post 20 can include a magnet socket 52 configured to house a magnet such as magnet 50 (see FIG. 8, for example). In some embodiments that include an HFO source, as shown in FIG. 3, an underside of sheet 25 can include ferromagnetic dome-shaped ring 62 that cooperates with magnet 50 to provide a continuous conduit such that fluid received from an HFO source at inlet 38 is delivered into the nostrils of the wearer via the respective opening in sheet 25. When magnet 50 is detachably attached to ferromagnetic dome-shaped ring 62 of sheet 25, the upper end of each post 20, i.e., exit ends 16, are in fluid communication with the interior of the nostrils of the wearer. The lower ends of post 20 are in fluid communication with the interior of nasal connector 90 such that respiratory fluid flows from exit end 16 (i.e., upper post opening) of each post 20 and through opening 17 of each sheet 25 and into the interior of the nostrils of the wearer. Thus, each post comprises a unique pathway for conveying fluid from a fluid source (for example, an HFO source with or without a HFNC) to the nasal passage of the patient. Magnet socket 52 is positioned about a first end of the post. In some embodiments that include an HFO source and/or a HFNC, magnet socket 52 (i.e., an upper surface of the post) can be angled in relation to post body 30 to allow for enhanced attachment to ferromagnetic dome-shaped ring 62 of sheet 25 for better positioning on the patient's nostrils (as illustrated, for example, in FIG. 20). Magnet socket 52, magnet 50 and opening 17 too can take various cross-sectional shapes. According to one or more embodiments that include an HFO source and/or a HFNC, an upper surface of the magnetic ring is angled. In such embodiments that include an HFO source and/or a HFNC, the magnetic ring can have different thicknesses in different regions of the magnetic ring.

Various embodiments of the presently disclosed subject matter can further allow a user to swap back and forth between an HFO source and a regular flow continuous positive airway pressure (CPAP) source based on the preferences of the end-user of the nasal respiratory assembly as disclosed herein. For example, an end-user may use the nasal respiratory assembly with a regular flow CPAP source when the end-user is healthy, and swap the regular flow CPAP source with a HFO source when the end-user is sick or is otherwise in need of increased supply of air/oxygen.

What is claimed is:

1. A nasal respiratory assembly comprising:
   a pair of sheets, each sheet defining an opening sized and shaped to fit over a nostril of a patient, with a ferromagnetic ring positioned at an underside of the sheet and circumferentially aligned with the opening having a passage in fluid communication with the opening, with an upper side of the sheet configured for sealable engagement with the nostril; and
   a connector comprising:
      a flange disposed at a sheet end thereof; and
      a pair of slip rings, each of the slip rings coupled to the flange about an outer circumferential perimeter portion,
      wherein each of the slip rings comprises:
         a magnet having a channel therethrough and an outer perimeter surface distal from the channel, and
         the magnet pivotally connected relative to the circumferential perimeter portion through an inner flexible sheet member disposed between and secured to the outer circumferential perimeter portion and the outer perimeter surface of the magnet,
         each magnet sized and shaped to be removably attachable to one of the ferromagnetic rings to form a substantially airtight connection therewith, and
      an inlet at a vent end that is in fluid communication with a flexible tubing connected to a fluid source on a first side, and the inlet is further in fluid communication with the opening of each of the pair of sheets through the channel of one of the magnets and a passage of one of the ferromagnetic rings on an opposed second side.

2. The assembly of claim 1, wherein the passage of the ferromagnetic ring has a round, oblong, oval or tear drop shaped cross-section, wherein the cross-section shape of the passage of the ferromagnetic ring matches a cross-section shape of the channel of the magnet.

3. The assembly of claim 1, further comprising a hollow elbow connecting the inlet at the vent end of the connector to the flexible tubing connected to the fluid source.

4. The assembly of claim 3, further comprising a swivel coupling connecting the hollow elbow to the flexible tubing.

5. The assembly of claim 3, wherein the hollow elbow comprises a fluid permeable exhaust through a portion of a surface of the hollow elbow and a first diffuser cap removably attached adjacent to the portion of the surface having the exhaust.

6. The assembly of claim 5, wherein one or more protrusions extending from the first diffuser cap frictionally engage one or more recessed notches defined along the surface of the hollow elbow when the first diffuser cap is removably attached to the hollow elbow.

7. The assembly of claim 3, wherein the hollow elbow comprises a fluid permeable exhaust through a portion of a surface of the hollow elbow, a first diffuser cap, and a second diffuser cap and wherein a rate of fluid flow from the hollow elbow through the exhaust is selectively adjusted based on one of the first diffuser cap and the second diffuser cap being removably attached adjacent to the portion of the surface having the exhaust.

8. The assembly of claim 1, wherein the magnet comprises a ridge extending radially outwardly from the outer perimeter surface to which the inner flexible sheet member is attached.

9. The assembly of claim 1, wherein the magnet comprises a groove extending radially inwardly from the outer perimeter surface into which a portion of the inner flexible sheet member is disposed and attached to the magnet.

10. The assembly of claim 1, wherein the passage and the channel have a cross section having an oblong shape.

11. The assembly of claim 1, wherein the passage and the channel have a cross section having an oval shape.

12. The assembly of claim 1, wherein the passage and the channel have a cross section having a teardrop shape.

13. The assembly of claim 1, wherein the outer circumferential perimeter portion of each of the slip rings has a round cross section and a predefined standard diameter.

14. A nasal respiratory assembly comprising:
   a pair of sheets, each sheet defining an opening sized and shaped to fit over a nostril of a patient, with a ferromagnetic ring positioned at an underside of the sheet and circumferentially aligned with the opening having a passage in fluid communication with the opening, with an upper side of the sheet configured for sealable engagement with the nostril; and
   a pair of hollow elbows, each of the pair of hollow elbows comprising a flange disposed at a sheet end thereof and a slip ring, the slip ring coupled to the flange about an outer circumferential perimeter portion,
      wherein the slip ring comprises:
         magnet having a channel therethrough and an outer perimeter surface distal from the channel, and
         the magnet being pivotally connected relative to the circumferential perimeter portion through an inner flexible sheet member disposed between and secured to the outer circumferential perimeter portion and the outer perimeter surface of the magnet, and the magnet sized and shaped to be removably attachable to one of the ferromagnetic rings to form a substantially airtight connection therewith, and an inlet at a vent end that is in fluid communication with a flexible tubing connected to a fluid source on a first side, and the channel of the magnet and the passage of one of the ferromagnetic rings connected on an opposed second side.

\* \* \* \* \*